US010472484B2

(12) United States Patent
Yiannikouris et al.

(10) Patent No.: US 10,472,484 B2
(45) **Date of Patent: *Nov. 12, 2019**

(54) AFLATOXIN TEMPLATES, MOLECULARLY IMPRINTED POLYMERS, AND METHODS OF MAKING AND USING THE SAME

(71) Applicant: Alltech, Inc., Nicholasville, KY (US)

(72) Inventors: Alexandros Yiannikouris, Lexington, KY (US); Thirupathi R. Yerramreddy, Lexington, KY (US); Joshua J. Martinez, Lexington, KY (US); Jeffrey R. Withers, Lexington, KY (US)

(73) Assignee: Alltech, Inc., Nicholasville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/869,152

(22) Filed: Jan. 12, 2018

(65) Prior Publication Data

US 2018/0163011 A1 Jun. 14, 2018

Related U.S. Application Data

(60) Continuation of application No. 15/235,283, filed on Aug. 12, 2016, now Pat. No. 9,902,830, and a division of application No. 14/613,562, filed on Feb. 4, 2015, now abandoned.

(51) Int. Cl.

| | |
|---|---|
| ***C08J 9/26*** | (2006.01) |
| ***C07D 311/78*** | (2006.01) |
| ***C07D 311/16*** | (2006.01) |
| ***B01J 20/26*** | (2006.01) |
| ***C08F 222/10*** | (2006.01) |

(52) U.S. Cl.

CPC ............... *C08J 9/26* (2013.01); *B01J 20/268* (2013.01); *C07D 311/16* (2013.01); *C07D 311/78* (2013.01); *C08F 222/1006* (2013.01); *C08F 2222/1013* (2013.01); *C08J 2201/0422* (2013.01); *C08J 2335/02* (2013.01)

(58) Field of Classification Search

CPC .......... B01J 20/268; C08J 9/26; C07D 311/16

See application file for complete search history.

(56) References Cited

U.S. PATENT DOCUMENTS

| | | | |
|---|---|---|---|
| 8,153,737 B2 | 4/2012 | Yiannikouris et al. | |
| 8,426,541 B2 | 4/2013 | Yiannikouris et al. | |
| 2002/0133072 A1 | 9/2002 | Wang et al. | |
| 2008/0038832 A1 | 2/2008 | Sellergren et al. | |
| 2011/0054132 A1* | 3/2011 | Yiannikouris | B01J 20/26 526/215 |
| 2012/0214897 A1 | 8/2012 | Yiannikouris et al. | |

FOREIGN PATENT DOCUMENTS

| | | |
|---|---|---|
| WO | 03101580 A1 | 12/2003 |
| WO | 2005075448 A2 | 8/2005 |

OTHER PUBLICATIONS

Prousis, K. C., et al., "FeCl3-catalyzed ultrasonic-assisted, solvent-free synthesis of 4-substituted coumarins . . . ," Ultrasonics Sonochemistry, 21 (2014) 937-942.

Alltech, Inc., "Design, Synthesis and efficacy evaluation of aflatoxin B1 analog template used for molecularly imprinted polymers production as possible high affinity and specificity sorptive material for aflatoxins", Poster displayed at the World Mycotoxin Forum (Nov. 10-12, 2014).

Ruckert B., et al., "Molecularly imprinted composite materials via iniferter-modified supports", J. Mater. Chem.; 12:2275-2280 (2002).

Sellergren, B., "Molecularly Imprinted Polymers: Man-made mimics of antibodies and their applications in analytical chemistry", Techniques and Instrumentation in Analytical Chemistry; vol. 23; Ed. Bone Sellergren (2001), pp. 1-4, 21-28, 41-45, 71-75, 203-212.

Yerramreddy, T. R., et al.,"Design, Synthesis and efficacy evaluation of aflatoxin B1 analog template used for molecularly imprinted polymers production as possible high affinity and specificity sorptive material for aflatoxins", Abstract from the World Mycotoxin Forum submitted Aug. 5, 2014 (1 page).

Zammarelli, N., et al., "Grafting-from Polymerization of PMMA from Stainless Steel Surfaces by a RAFT-Mediated Polymerization Process" Langmuir; 29:12834-12843 (2013).

Gultek, A., et al., "Poly(methacrylic) Acid and gamma-methacryloxypropyltrimethoxy Silane/Clay Nanocomposites Prepared by In-Situ Polymerization" Turk J Chem.; 26:925-937 (2002).

Trost, Barry M et al., "Palladium Catalyzed Kinetic and Dynamic Kinetic Asymmetric Transformations of γAcyloxybutenolides. Enantioselective Total Synthesis of (+)-Aflatoxin B1 and B2a" Journal of the American Chemical Society, 2003, 125(10), p. 3090-3100.

Bhute, R.S. et al., "Synthesis of 5,7-Dimethoxycyclopentenone-[2,3c]coumarin" Indian Journal of Chemistry, 1966, 4(2), p. 96-97.

Szumski, Michal et al., "Monolithic molecularly imprinted polymeric capillary columns for isolation of aflatoxins" Journal of Chromatography A, 2014, 1364, p. 163-170.

Wyszomirski, Miroslaw et al., "Molecular modelling of a template substitute and monomers used in molecular imprinting for aflatoxin BI micro-HPLC analysis" Molecular Simulation, Sep. 2012, 38(11), p. 892-895.

Notice of Reasons for Rejection for Japanese Patent Application No. 2015-020396, issued by the Japan Patent Office, dated Sep. 5, 2018, including an English-language translation, 17 pages.

Examination Report for Indian Patent Application No. 560/CHF/215, issued by Intellectual Property India, dated Jul. 26, 2018, 7 pages.

Substantive Examination Adverse Report for Malaysia Patent Application No. PI 2015000273, issued by the Intellectual Property Corporation of Malaysia, dated Aug. 15, 2018, including a Search Report, 3 pages.

Office Action for Israel Patent Application No. 237090, issued by the Israel Patent Office, dated Jun. 19, 2018, including English-language translation, 6 pages.

* cited by examiner

*Primary Examiner* — Robert C Boyle

(74) *Attorney, Agent, or Firm* — Kilyk & Bowersox, P.L.L.C.

(57) ABSTRACT

Molecularly imprinted polymers (MIPs) are materials exhibiting molecular recognition of a target molecule. MIPs are synthesized in the presence of an aflatoxin template, a mimic to the targeted molecule, used as an imprint that is further washed away with suitable solvent after completion of the polymerization process, leaving a cavity in the polymer of the same stereochemistry, functionality and morphology to the template. When the MIP encounters an aflatoxin, the molecule is bound in the cavity with a receptor-like affinity.

12 Claims, 5 Drawing Sheets

Scheme-1

AFLATOXIN TEMPLATES, MOLECULARLY IMPRINTED POLYMERS, AND METHODS OF MAKING AND USING THE SAME

This application is a continuation of U.S. patent application Ser. No. 15/235,283, filed Aug. 12, 2016, now pending, which in turn is a divisional of U.S. patent application Ser. No. 14/613,562, filed Feb. 4, 2015, now abandoned, which are incorporated in their entireties by reference herein.

FIELD OF THE DISCLOSURE

The disclosure relates generally to Aflatoxin templates and molecularly imprinted polymers (MIPs). In particular, the disclosure relates to reusable, ecologically friendly MIPs, methods of producing the same, and methods of utilizing the same (e.g., to sequester and/or adsorb aflatoxins). Compositions and methods of the disclosure find use in a variety of applications including dietary, therapeutic, prophylactic, food and beverage processing and manufacture, as well as research and quality control applications.

BACKGROUND

Mycotoxins are secondary metabolites secreted by a variety of fungi, often produced in cereal grains as well as forages before, during and after harvest. Forages and cereals naturally come into contact with fungal spores. The fungal contamination of plants and the bio-synthesis of toxins depend on the state of health of the plant before harvest, meteorological conditions, harvesting techniques, delays and hydrothermal conditions before stabilization for conservation and feed processing. Depending on the fungus, fungal growth is controlled by a number of physico-chemical parameters including the amount of free water ($a_w$), temperature, presence of oxygen, nature of the substrate, and pH conditions. Mycotoxins proliferate pre-harvest as well as post-harvest in storage.

Some fungi produce toxins only at specific levels of moisture, water availability, temperature or oxygen. The effects of mycotoxins vary greatly in their severity. Some mycotoxins are lethal, some cause identifiable diseases or health problems, some weaken the immune system without producing symptoms specific to that mycotoxin, some act as allergens or irritants, and some have no known effect on animals or humans. According to recent United Nation's Food and Agriculture Organization (FAO) reports, approximately 25% of the world's grain supply is contaminated with mycotoxins. Mycotoxin contamination has a negative economic impact on food and feed producers, particularly grain and animal producers.

Mycotoxins can appear in the food chain as a result of fungal infection of plant products (e.g., forage, grain, plant protein, processed grain by-products, roughage and molasses products), and can either be eaten directly by humans, or introduced by contaminated grains, livestock or other animal feedstuff(s). Mycotoxins greatly resist decomposition during digestion so they remain in the food chain in edible products (e.g., meat, fish, eggs and dairy products) or under the form of metabolites of the parent toxin ingested. Temperature treatments such as cooking and freezing are not adequate methods of decreasing the prevalence of mycotoxins. Thus, there exists a need for compositions and/or methods for reducing the detrimental effects and/or eliminating mycotoxin occurrence in feed and/or food chains.

Aflatoxins are members of the mycotoxin family. These toxins are produced by moulds of the *Aspergillus* sp. such as *Aspergillus flavus* or *A. Parasiticus* that contaminate a variety of feed and food materials and that can ultimately transfer in their native form or has metabolites in animal by-products such as milk, eggs or potentially meat. Aflatoxins represent a significant health risk due to their high toxicity and carcinogenicity and regulatory levels are strictly enforcing their acceptable concentration in animal feeds and human food.

SUMMARY

There is a need for isolation of aflatoxins and metabolites from materials both for diagnostic and mitigation purposes. Molecularly imprinted polymers (MIPs) as described herein are materials exhibiting molecular recognition of an aflatoxin. MIPs are synthesized in the presence of an aflatoxin template (e.g. a mimic of aflatoxin), which is used to make an imprint and then is removed from the polymer after completion of the polymerization process, leaving a cavity in the polymer of the same stereochemistry, functionality, and morphology of the template. When the MIP encounters the aflatoxin, the aflatoxin is bound in the cavity.

The present disclosure relates generally to aflatoxin templates and molecularly imprinted polymers (MIPs). In particular, the disclosure relates to reusable, ecologically friendly MIPs, methods of producing the same, methods of utilizing the same (e.g., to sequester and/or adsorb aflatoxins), and methods for applying the use in different ways (e.g., to detect presence of aflatoxins for traceability purposes and to remove aflatoxins from a contaminated source). Compositions and methods of the disclosure find use in a variety of applications including dietary, therapeutic, prophylactic, food and beverage processing and manufacture, liquid filtering as well as research and quality control applications.

In embodiments, aflatoxin templates, monomers, crosslinkers, and/or MIPs have favorable safety and/or environmental properties such as reduced or no toxicity, and high water sorption, and retention of aflatoxins. In preferred embodiments, MIPs can be reusable and economically realizable/producible.

In one aspect of the disclosure, aflatoxin templates are provided. In a particular embodiment, an aflatoxin template has a Formula (I):

(I)

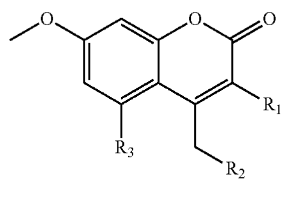

wherein $R_1$ is selected from H, $C_{1-6}$ alkyl, substituted $C_{1-6}$ alkyl, and a halo substituted $C_{1-6}$ alkyl; $R_2$ is selected from halo, $C_{1-6}$ alkyl, substituted $C_{1-6}$ alkyl, a halo substituted $C_{1-6}$ alkyl, $CH_2C(O)OR'$, and $CH(C(O)OR')_2$; wherein R' is selected from H, $C_{1-6}$ alkyl, and substituted $C_{1-6}$ alkyl; and $R_3$ is selected from H, $C_{1-6}$ alkoxy, and substituted $C_{1-6}$ alkyl. In embodiments, R' further comprises substituents selected from a group consisting of halo, hydroxy and alkoxy. In a specific embodiment, an aflatoxin template is an isolated compound that has a Formula of:

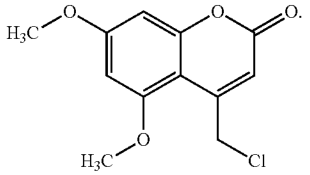 [SMILES: COc1cc(OC)c2c(CCl)cc(=O)oc2c1]

Additional embodiments include aflatoxin templates that have a formula selected from the group consisting of:

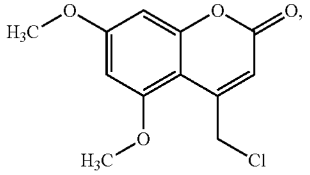

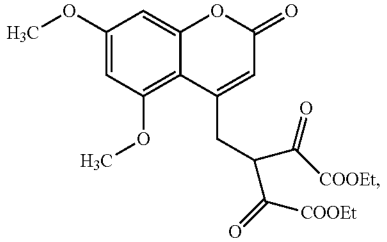

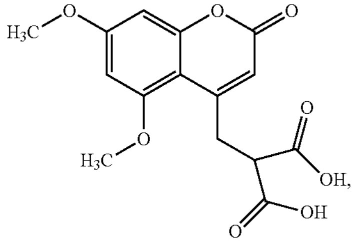

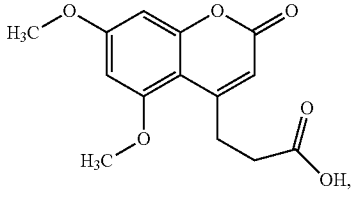

and combinations thereof.

Another aspect of the disclosure includes a method of synthesis of an aflatoxin template of Formula (1) comprising: reacting 3,5-dimethoxy phenol with ethyl 4-chloroacetoacetate in acid to form 4-(chloromethyl)-5,7-dimethoxy coumarin.

In other embodiments, a method of synthesis of an aflatoxin template comprises suspending a monoacid according to the Formula of:

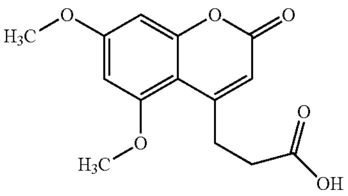 [SMILES: COc1cc(OC)c2c(CCC(=O)O)cc(=O)oc2c1]

in polyphosphoric acid and heating to at least 50° C.; cooling the reaction mixture below 50° C. and adding an aqueous solution to obtain an aflatoxin template according to the Formula of:

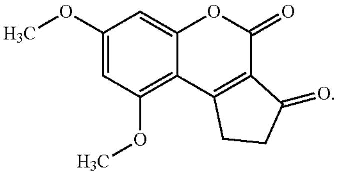 [SMILES: COc1cc(OC)c2c3c(c(=O)oc2c1)C(=O)CC3]

In other embodiments, a monoacid is provided by suspending a diacid according to a Formula of:

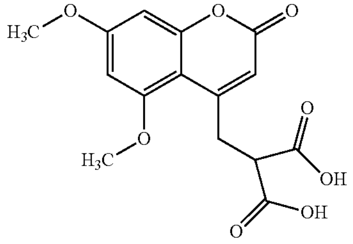 [SMILES: COc1cc(OC)c2c(CC(C(=O)O)C(=O)O)cc(=O)oc2c1]

in a solvent and heating to at least 100 to 140° C.

In another embodiment, a method of synthesis of an aflatoxin template compound comprises: deprotecting a diethyl intermediate propanedioic acid, 2-[(5,7-dimethoxy-2-oxo-2H-1-benzopyran-4-yl)methyl]-, 1,3-diethyl ester to form a diacid analog; and precipitating the diacid analog to isolate the aflatoxin template with the Formula of:

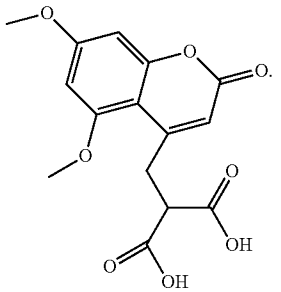 [SMILES: COc1cc(OC)c2c(CC(C(=O)O)C(=O)O)cc(=O)oc2c1]

In other embodiments, a propanedioic acid, 2-[(5,7-dimethoxy-2-oxo-2H-1-benzopyran-4-yl)methyl]-, 1,3-diethyl ester is prepared by a method comprising: combining 4-(chloromethyl)-5,7-dimethoxy coumarin with diethyl malonate, potassium iodide, and a crown ether in a polar solvent to form a mixture; and adding potassium butoxide to the mixture to form propanedioic acid, 2-[(5,7-dimethoxy-2-oxo-2H-1-benzopyran-4-yl)methyl]-, 1,3-diethyl ester.

In other embodiments, a method of synthesis of an aflatoxin template of Formula (I) comprises: deprotecting propanedioic acid, 2-[(5,7-dimethoxy-2-oxo-2H-1-benzopyran-4-yl)methyl]-, 1,3-diethyl ester to form a diacid analog, and precipitating the diacid analog of Formula:

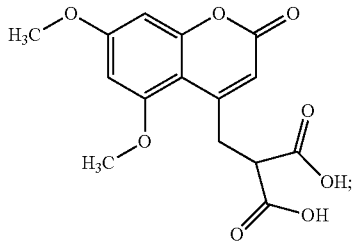 [SMILES: COc1cc(OC)c2c(CC(C(=O)O)C(=O)O)cc(=O)oc2c1]

Suspending the diacid analog in a solvent, heating to at least 100 to 140° C., and precipitating the monoacid of Formula:

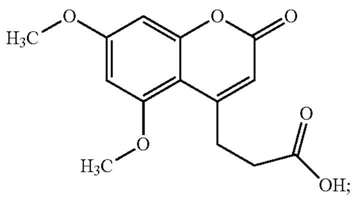 [SMILES: COc1cc(OC)c2c(CCC(=O)O)cc(=O)oc2c1]

Suspending the monoacid in an acid and heating to at least 50° C., cooling the reaction mixture to below 50° C., and adding an aqueous solution to obtain a compound of Formula:

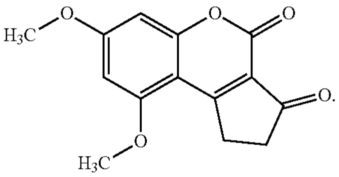 [SMILES: COc1cc(OC)c2c3c(c(=O)oc2c1)C(=O)CC3]

Another aspect of the disclosure provides a molecularly imprinted polymer intermediate comprising a complex of a crosslinked polymer made from a monomer and an aflatoxin template having a Formula (I) of:

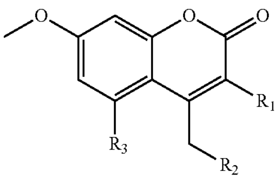

wherein $R_1$ is selected from H, $C_{1-6}$ alkyl, substituted $C_{1-6}$ alkyl, and a halo substituted $C_{1-6}$ alkyl; $R_2$, is selected from halo, $C_{1-6}$ alkyl, substituted $C_{1-6}$ alkyl, a halo substituted $C_{1-6}$ alkyl, $CH_2C(O)OR'$, and $CH(C(O)OR')_2$; wherein R' is selected from H, $C_{1-6}$ alkyl, and substituted $C_{1-6}$ alkyl; and $R_3$, is selected from H, $C_{1-6}$ alkoxy, and substituted $C_{1-6}$ alkyl, or wherein $R_1$ together with $R_2$ form a $C_{4-7}$ cycloalkyl ring, a halo substituted $C_{4-7}$ cycloalkyl ring, an oxo substituted $C_{4-7}$ cycloalkyl ring, a $C_{4-7}$ cycloalkoxy ring a hydroxyl substituted $C_{4-7}$ cycloalkyl ring, or a carboxylic group substituted $C_{4-7}$ cycloalkyl; and $R_3$ is selected from H, $C_{1-6}$ alkoxy, and substituted $C_{1-6}$ alkyl. In particular embodiments, the molecularly imprinted polymer intermediate has an aflatoxin template to monomer ratio from about 100:1 to 1:100. In other embodiments, the molecularly imprinted polymer intermediate has a monomer to crosslinker ratio from about 1:4.1 to 1:10. In yet other embodiments, the molecularly imprinted polymer intermediate includes an aflatoxin template of Formula (I) selected from the group consisting of 4-(chloromethyl)-5,7-dimethoxy coumarin, 5,7-dimethoxycyclo pentenon[2,3-c]coumarin, and combinations thereof.

Another aspect of the disclosure includes a molecularly imprinted polymer comprising a crosslinked polymer made from a monomer, wherein the polymer has a plurality of cavities, wherein at least one of the cavities was made using the aflatoxin template having a Formula (I) of:

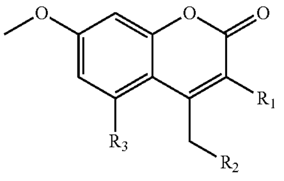

wherein $R_1$ is selected from H, $C_{1-6}$ alkyl, substituted $C_{1-6}$ alkyl, and a halo substituted $C_{1-6}$ alkyl; $R_2$ is selected from halo, $C_{1-6}$ alkyl, substituted $C_{1-6}$ alkyl, a halo substituted $C_{1-6}$ alkyl, $CH_2C(O)OR'$, and $CH(C(O)OR')_2$; wherein R' is selected from H, $C_{1-6}$ alkyl, and substituted $C_{1-6}$ alkyl; and $R_3$ is selected from H, $C_{1-6}$ alkoxy, and substituted $C_{1-6}$ alkyl, or wherein $R_1$ together with $R_2$ form a $C_{4-7}$ cycloalkyl ring, a halo substituted $C_{4-7}$ cycloalkyl ring, an oxo substituted $C_{4-7}$ cycloalkyl ring, a $C_{4-7}$ cycloalkoxy ring a hydroxy substituted $C_{4-7}$ cycloalkyl ring, or a carboxylic group substituted $C_{4-7}$ cycloalkyl; and $R_3$ is selected from H, $C_{1-6}$ alkoxy, and substituted $C_{1-6}$ alkyl. In particular embodiments, the molecularly imprinted polymer includes an aflatoxin template that is 4 (chloromethyl)-5,7-dimethoxy coumarin. In embodiments, the molecularly imprinted polymer includes an aflatoxin template compound that is 5,7-dimethoxycyclo pentenon[2,3-c]coumarin. In embodiments, a molecularly imprinted polymer has a monomer that is selected from the group consisting of methacrylic acid, 2-vinylpyridine, 2-hydroxyethylmethacrylate and combinations thereof. In embodiments, a molecularly imprinted polymer has a crosslinker that is ethylene glycol dimethacrylate. In yet other embodiments, the molecularly imprinted polymer has aflatoxin template to monomer ratio that is from about 100:1 to 1:100. In yet other embodiments, the molecularly imprinted polymer has a monomer to crosslinker ratio that is from about 1:4.1 to 1:10.

Another aspect of the disclosure includes a method of making a molecularly imprinted polymer comprising the steps of: providing an aflatoxin template having a Formula (I) of:

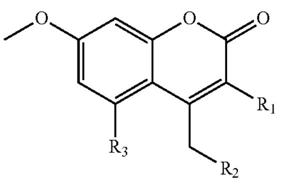

wherein $R_1$ is selected from H, $C_{1-6}$ alkyl, substituted $C_{1-6}$ alkyl, and a halo substituted $C_{1-6}$ alkyl; $R_2$ is selected from halo, $C_{1-6}$ alkyl, substituted $C_{1-6}$ alkyl, a halo substituted $C_{1-6}$ alkyl, $CH_2C(O)OR'$, and $CH(C(O)OR')_2$; wherein R' is selected from H, $C_{1-6}$ alkyl, and substituted $C_{1-6}$ alkyl; and $R_3$ is selected from H, $C_{1-6}$ alkoxy, and substituted $C_{1-6}$ alkyl, or wherein $R_1$ together with $R_2$ form a $C_{4-7}$ cycloalkyl ring, a halo substituted $C_{4-7}$ cycloalkyl ring, an oxo substituted $C_{4-7}$ cycloalkyl ring, a $C_{4-7}$ cycloalkoxy ring, a hydroxy substituted $C_{4-7}$ cycloalkyl ring, or a carboxylic group substituted $C_{4-7}$ cycloalkyl; and $R_3$ is selected from H, $C_{1-6}$ alkoxy, and substituted $C_{1-6}$ alkyl; combining the aflatoxin template with at least one monomer and one or more crosslinkers; polymerizing the monomer and the one or more crosslinkers to form a molecularly imprinted polymer intermediate; and removing the aflatoxin template from the molecularly imprinted polymer intermediate to form a molecularly imprinted polymer. In particular embodiments, the aflatoxin template comprises 5,7-dimethoxy-cyclopentenon [2,3-c]coumarin 4-(chloromethyl)-5,7-dimethoxy coumarin, or combinations thereof. In embodiments, an MIP is prepared by a process as described herein.

In embodiments, the step of combining of aflatoxin template compound with at least one monomer and one or more crosslinkers comprises mixing the monomer and the crosslinker in a solution of one or more organic solvents. In particular embodiments, the one or more solvents are selected from the group consisting of acetonitrile, toluene, cyclohexane, polyvinyl alcohol in water solution, and a mixture of two or more of acetonitrile, toluene, cyclohexane, polyvinyl alcohol in water solution.

In other embodiments, a method further comprises adding an initiator. In a particular embodiment, the initiator is azo(bis)-isobutyronitrile (AIBN), wherein free radicals are formed by thermal decomposition of AIBN acting as an initiator. In yet other embodiments, polymerization is initiated by forming free radicals in an organic solvent at a temperature between 55 and 110° C.

In embodiments, the removal of the aflatoxin template from the molecularly imprinted polymer intermediate comprises washing the molecularly imprinted polymer intermediate with a solvent. In particular embodiments, the organic solvent is selected from the group of ethyl alcohol, methyl alcohol, acetonitrile, toluene, and a mixture of thereof.

In embodiments, the molecularly imprinted polymer is dried after said one or more washes.

Another aspect of the disclosure includes a method of sequestering an aflatoxin comprising: providing a molecularly imprinted polymer having a plurality of cavities, wherein at least one of the cavities is made using the aflatoxin template having a Formula (I) of:

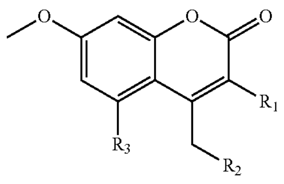

wherein $R_1$ is selected from H, $C_{1-6}$ alkyl, substituted $C_{1-6}$ alkyl, and a halo substituted $C_{1-6}$ alkyl; $R_2$ is selected from halo, $C_{1-6}$ alkyl, substituted $C_{1-6}$ alkyl, a halo substituted $C_{1-6}$ alkyl, $CH_2C(O)OR'$, and $CH(C(O)OR')_2$; wherein R' is selected from H, $C_{1-6}$ alkyl, and substituted $C_{1-6}$ alkyl; and $R_3$ is selected from H, $C_{1-6}$ alkoxy, and substituted $C_{1-6}$ alkyl, or wherein $R_1$ together with $R_2$ form a $C_{4-7}$ cycloalkyl ring, a halo substituted $C_{4-7}$ cycloalkyl ring, an oxo substituted $C_{4-7}$ cycloalkyl ring, a $C_{4-7}$ cycloalkoxy ring, a hydroxy substituted $C_{4-7}$ cycloalkyl ring, or a carboxylic group substituted $C_{4-7}$ cycloalkyl; and $R_3$ is selected from H, $C_{1-6}$ alkoxy, and substituted $C_{1-6}$ alkyl; providing a material, wherein the material optionally contains an aflatoxin; and contacting the molecularly imprinted polymer with the material.

In embodiments, the material is a liquid, a solid, or a gas. In particular embodiments, the material is selected from the group consisting of soil, a spice, a beverage, a foodstuff, an animal feed, a pharmaceutical composition, a nutraceutical composition, and a cosmetic composition. In a specific embodiment, the material is milk.

In embodiments, the molecularly imprinted polymer is contacted with the material for at least 1 second.

In embodiments, a method further comprises separating the molecularly imprinted material from the material. In particular embodiments, the separation of the molecularly imprinted polymer comprises separating by filtration or by centrifugation.

In embodiments, a method further comprises detecting an amount of aflatoxin complexed with the molecularly imprinted polymer, detecting the amount of aflatoxin in the material after contact with the molecularly imprinted polymer, or both.

In other embodiments, a method of sequestering an aflatoxin comprises steps of: providing a molecularly imprinted polymer having a plurality of cavities, wherein at least one cavity was made using an aflatoxin template having a Formula (I) of:

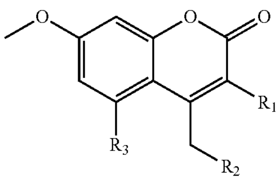

wherein $R_1$ is selected from H, $C_{1-6}$ alkyl, substituted $C_{1-6}$ alkyl, and a halo substituted $C_{1-6}$ alkyl; $R_2$ is selected from halo, $C_{1-6}$ alkyl, substituted $C_{1-6}$ alkyl, a halo substituted $C_{1-6}$ alkyl, $CH_2C(O)OR'$, and $CH(C(O)OR')_2$; wherein R' is selected from H, $C_{1-6}$ alkyl, and substituted $C_{1-6}$ alkyl; and $R_3$ is selected from H, $C_{1-6}$ alkoxy, and substituted $C_{1-6}$ alkyl, or wherein $R_1$ together with $R_2$ form a $C_{4-7}$ cycloalkyl ring, a halo substituted $C_{4-7}$ cycloalkyl ring, an oxo substituted $C_{4-7}$ cycloalkyl ring, a $C_{4-7}$ cycloalkoxy ring, a hydroxy substituted $C_{4-7}$ cycloalkyl ring, or a carboxylic group substituted $C_{4-7}$ cycloalkyl; and $R_3$ is selected from H, $C_{1-6}$ alkoxy, and substituted $C_{1-6}$ alkyl; b) providing a material containing an aflatoxin; and c) contacting the molecularly imprinted polymer with the material, wherein the molecularly imprinted polymer sequesters at least 40 percent of the aflatoxin by weight per unit of the material. In embodiments, the material is a liquid and the molecularly imprinted polymer sequesters at least 40 percent of the weight of aflatoxin per volume of the material.

DEFINITIONS

Figure 1:
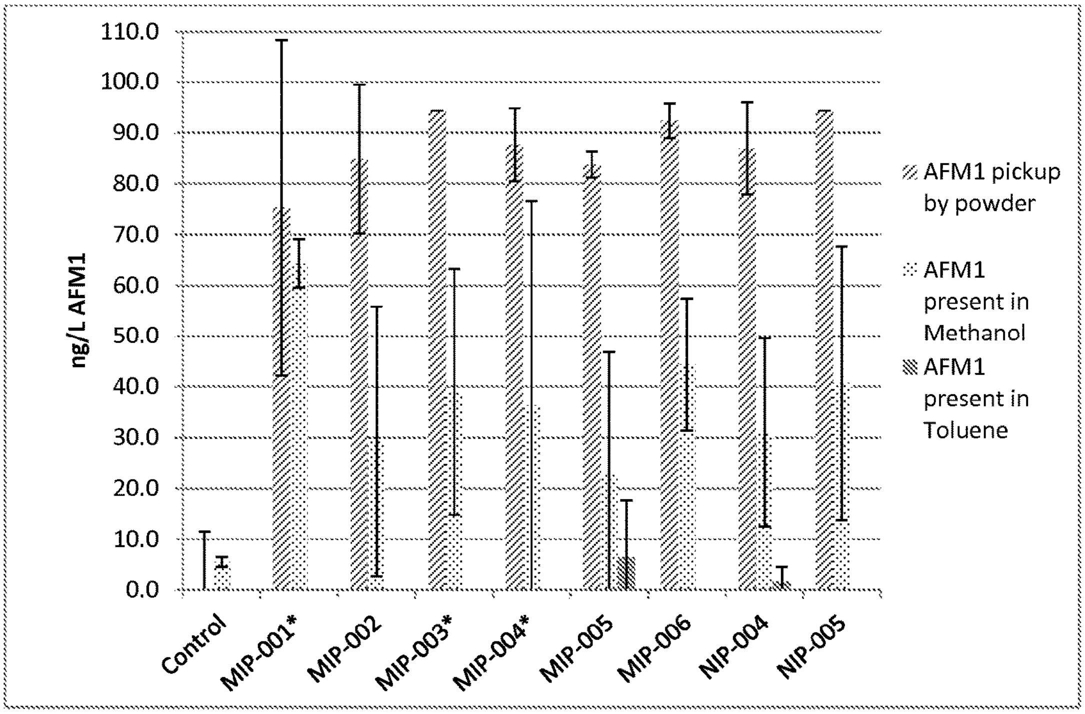
FIG. 1 shows the quantity of aflatoxin M1 (AFM1) adsorbed by 1 mg quantity of each MIP in an instant trapping solid phase extraction (SPE) column setup using 1 mL of a 100 ng/L solution of AFM1 in a pH 6.0 ammonium acetate buffer (▒). Also shown are the quantities of AFM1 present in subsequent methanol (░) and toluene (■) washed performed after the adsorption step. Quantity of AFM1 adsorbed vs. quantity of AFM1 released from the material can be quantified.

As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

As used herein, the term "molecularly imprinted polymer (s)" or "MIP(s)" refers to synthetic polymers that selectively bind to one or more aflatoxins. In embodiments, a MIP exhibits high enantioselectivity and low substrate selectivity, wherein the MIP interacts with the template aflatoxin racemate as well as its corresponding analogs, such as naturally occurring aflatoxins. In embodiments, the MIP has a higher enantioselectivity than the corresponding non-imprinted polymer for the binding of aflatoxins. In embodiments, the MIP selectively binds to aflatoxins and does not bind to other mycotoxins. In embodiments, the MIP binds to one or more of aflatoxins B1, B2, G1, G2, M1, M2, P1, and Q1. In embodiments, the MIP selectively binds aflatoxin B1 and aflatoxin M1.

In embodiments, a polymer is crosslinked to generate cavities, at least one of which is made using an aflatoxin template of Formula (I). In some embodiments, at least one cavity provides a site of interaction for reversible binding with an aflatoxin template of Formula (I) and/or aflatoxins. In general, MIPs are constructed using: i) a templates (e.g., aflatoxin template) that mimic the structure, size, shape and/or other chemical characteristics of one or more targeted compound(s) (e.g., aflatoxins) and ii) other components, such as monomers and/or cross linking reagents. For example, one or more aflatoxin templates are incorporated into a pre-polymeric mixture comprising monomers and a crosslinker. The mixture is then polymerized to form a "molecularly imprinted polymer intermediate" or "MIP intermediate" comprising a crosslinked polymer and the aflatoxin template(s). Once the polymer has formed, the aflatoxin template(s) is/are removed, leaving behind complementary cavities having a chemical and/or physical capacity to form a complex with one or more aflatoxins or other compounds resembling aflatoxin. Such regions (e.g., cavities or other regions) are tailored for binding one or more aflatoxins giving rise to a high affinity for such aflatoxin containing compounds and selectivity. While aflatoxin template compounds are used to form molecularly imprinted polymers, in some embodiments, the MIPs may have a high affinity for a class of compounds that is distinct from but similar to one or more aflatoxins. For example, a MIP may bind a number of compounds containing molecules that are similar in shape, size, charge density, geometry or other physical or chemical properties to one or more aflatoxins.

As used herein, the term "non-imprinted polymer" or "NIP" refers to synthetic polymers that are formed without the presence of a template compound (e.g., aflatoxin template). Such polymers, which have no enantioselectivity nor substrate selectivity, and might interact with any molecules susceptible to generate hydrogen-bounding, ionic interaction, electrostatic interaction with the components of the NIP. NIPs are involved in non-specific non-covalent surface interactions of lower stability than when a specific cavity is available from the imprinting process in the MIP network to target a specific compound (e.g., AFB1, AFM1). In embodiments, a "corresponding" NIP refers to a synthetic polymer synthesized with the same monomer and crosslinker as a MIP but without the use of a template (e.g., aflatoxin template).

As used herein, the term "polymer", refers to a molecule (macromolecule) composed of repeating structural units (e.g. monomer) typically connected by covalent chemical bonds forming a network. In embodiments, a polymer is formed by crosslinking of monomers forming primary chains or structural units that assemble in a network.

As used herein, the term "aflatoxin template(s)" refer(s) to one or more synthetically constructed molecule(s) that mimic the structure, size, shape and/or other chemical characteristics of one or more natural aflatoxins. The disclosure is not limited by the type of aflatoxin template utilized, that can be either synthetic or natural. Indeed a variety of aflatoxins may bind to MIPs generated using an aflatoxin template compound including, but not limited to, aflatoxin B1, B2, G1, G2, M1, P1, Q1, and other aflatoxins described herein.

As used herein, the term "monomer(s)", refers to a molecule that may become chemically bonded to other monomers to form a polymer.

As used herein, the terms "crosslink" and "crosslinker", refer to molecules that contain two, three or four double-bonds that are capable of attaching to two or more monomers to form a polymer network.

As used herein, the term "structural unit", refers to a building block of a polymer chain, and related to the repeat unit.

As used herein, the term "anionic" or "anion" refers to an ion that has a negative charge.

As used herein, the term "cationic" or "cation" refers to an ion that has a positive charge. This term can refer to polymeric compounds, such as molecularly imprinted polymers, that contain a positive charge.

As used herein, the term "acid" as used herein refers to any chemical compound that can donate proton(s) and/or accept electron(s). As used herein, the term "base" refers to any chemical compound that can accept proton(s) and/or donate electron(s) or hydroxide ions. As used herein, the term "salt" refers to compounds that may be derived from inorganic or organic acids and bases.

As used herein, the term "bleeding", refers to a remaining fraction of the template still in association with the MIP after several washing stages of the MIP, and that continues to dissociate from the MIP and interfere with its adsorption activity.

As used herein, the term "porogenic/porogen", refers to a substance, molecule, buffer, solvent, (e.g., toluene, xylene, ethylbenzene) used to change the size of the cavities in a polymer (e.g., cavities of a MIP). In embodiments, a polymer to porogen ratio is directly correlated to the amount of porosity of the final structure and dictates the size of the polymer agglomerates formed.

As used herein, the term "inclusion rate" refers to the amount of MIP provided per unit of material (e.g. milk), for example, in a unit of weight of the polymer as compared to a unit of volume of the material or in a unit of weight of the polymer as compared to a unit per weight of the material.

As used herein, the term "cavity(ies)", refer(s) to a space, pore, or other opening that is/are within the MIP and that are sized and/or shaped to allow an aflatoxin to be bound therein. In embodiments, a cavity is formed in a crosslinked polymer by polymerizing the polymer in the presence of the aflatoxin template and removing the aflatoxin template to form the cavity in the crosslinked polymer, which is now an MIP.

As used herein, the term "polymerization", refers to a process of reacting monomer molecules together in a chemical reaction to form three-dimensional networks or polymer chains and agglomerated polymers chains.

As used herein, the term "precipitation", refers to the formation of a solid in a solution during a chemical reaction. When the reaction occurs, the solid formed is called the precipitate, and the liquid remaining above the solid is called the supernatant.

As used herein, the term "centrifugation" refers to the process of separating molecules by size or density using centrifugal forces generated by a spinning rotor that puts an object in rotation around a fixed axis, applying a force perpendicular to the axis. The centrifuge works using the sedimentation principle, where the centripetal acceleration is used to evenly distribute substances of greater and lesser density into different layers of density.

As used herein, the term "concentration" refers to the amount of a substance per defined space. Concentration usually is expressed in terms of mass per unit of volume. To dilute a solution, one must add more solvent, or reduce the amount of solute (e.g., by selective separation, evaporation, spray drying, freeze drying). By contrast, to concentrate a solution, one must reduce the amount of solvent.

As used herein, the term "layer" refers to a usually horizontal deposit organized in stratum of a material forming an overlying part or segment obtained after separation by centrifugation or sedimentation in relation with the density properties of the material.

As used herein, the term "purified" or "to purify" refers to the removal of foreign components from a sample. When used in a chemical context "purified" or "to purify" refers to the physical separation of a chemical substance of interest from undesired substances. Commonly used methods for purification of organic molecules, include, but are not limited to the following: affinity purification, mechanical filtration, centrifugation, evaporation, extraction of impurity, dissolving in a solvent in which other components are insoluble, crystallization, adsorption, distillation, fractionation, sublimation, smelting, refining, electrolysis and dialysis.

As used herein, the term "drying" refers to any kind of process that reduces or eliminates the amount of liquid in a substance.

As used herein, the term "washing" refers to the removal (e.g., using any type of solute (e.g., distilled water, buffer, or solvent, or mixture)) of impurities or soluble unwanted component of a preparation (e.g., a MIP may be washed to remove the aflatoxin template components from the sample).

As used herein, the term "analyte" refers to an atom, a molecule, a substance, or a chemical constituent. In general, an analyte, in and of itself is not measured, rather, aspects or properties (physical, chemical, biological, etc.) of the analyte are determined using an analytical procedure, such as Ultra Performance Liquid Chromatography (abbreviated as UPLC). For example, in general one does not measure a "chair" (analyte-component) in and of itself, but, the height, width, etc. of a chair are measured. Likewise, in general one does not measure an aflatoxin but rather measures one or more properties of the aflatoxin (e.g., aflatoxins fluorescence or molecular weight, related for example, to its stability, concentration, or biological activity).

As used herein, the term "sample" is used in a broad sense including a specimen from any source (e.g., synthetic, biological and environmental samples). Synthetic samples include any material that is artificially produced (e.g., MIP). Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples.

As used herein, the term "Ultra Performance Liquid Chromatography" or "UPLC" refers to a form of liquid chromatography to separate compounds. The compounds are dissolved in a solution. Compounds are separated by injecting a sample mixture onto a column, through which a solvent or solvent mixture has been flowing at a specific pressure, to elute components of the mixture, from the column. UPLC instruments comprise one or more reservoirs of mobile phases, a pump, an injector, a separation column, and a detector. The presence of analytes in the column effluent is recorded by quantitatively detecting a change in refractive index, UV-VIS absorption at a set wavelength, fluorescence after excitation with a suitable wavelength, electrochemical response, or mass to charge ratio based on the molecular weight of an analyte in a charged state.

As used herein, the term "signal" is used generally in reference to any detectable process that indicates that a reaction has occurred (for example, binding of antibody to antigen). Signals can be assessed qualitatively as well as quantitatively. Examples of types of"signals" include, but are not limited to, radioactive signals, fluorometric signals, colorimetric product/reagent signals, mass to charge ratio measure.

As used herein, the terms "absorb" and "absorption" refer to the process by which a material "takes in" or "sucks up" another substance. For example, "absorption" may refer to the process of taking in or assimilating substances into cells or across the tissues and organs through diffusion or osmosis (e.g., absorption of nutrients by the digestive system or absorption of drugs into the blood stream).

As used herein, the terms "adsorb" and "adsorption" refer to a process that occurs when a material is captured by, sequestered by, bound by, trapped by, and/or accumulated by (e.g., on the surface of) a composition (adsorbent), or to a process in which a composition (e.g., MIP) binds to a target molecule (e.g., one or more aflatoxins) in a sample (e.g., for removing the target molecule from a sample).

As used herein, the terms "sorb" and "sorption" refer to both adsorption and absorption.

As used herein, the terms "sequester", "capture", "trap", "adsorb", or "bind" refer to physical association (e.g., via bonding (e.g., hydrogen boding, ionic bonding, covalent bonding or other type of bonding) of two or more entities that come into contact with one another (e.g., thereby forming a complex). Exemplary forms of associations include, but are not limited to, hydrogen bonding, coordination, and ion pair formation. Sequestering interactions may involve a variable number of chemical interactions (e.g., chemical bonds) depending on the stereochemistry and geometry of each entity (e.g., further defining the specificity of the sequestering). When two or more entities are interacting they may be sequestered by way of chemical bonds or physical bonds but may also be associated via charge, dipole-dipole or other type of interactions.

As used herein, the terms "sequestering agent", "capturing agent", "trapping agent", "adsorbing agent" and/or "binding agent", refer to an entity that is capable of forming a complex with a second entity.

As used herein, the term "complex" refers to an entity formed by association between two or more separate entities (e.g., association between two or more entities wherein the entities are the same or different (e.g., same or different chemical species).

The association may be via a covalent bond or a non-covalent bond (e.g., via van der Waals, electrostatic, charge interaction, hydrophobic interaction, dipole interaction, and/or hydrogen bonding forces (e.g., urethane linkages, amide linkages, ester linkages, and combination thereof)).

As used herein, the term "bind" refers to a close association between two or more separate entities (e.g., association between two or more entities wherein the entities are the same or different (e.g., same or different chemical species). The association may be via a covalent bond or a non-covalent bond (e.g., via van der Waals, electrostatic, charge interaction, hydrophobic interaction, dipole interaction, and/or hydrogen bonding forces (e.g., urethane linkages, amide linkages, ester linkages, and combination thereof)). As used herein, the term "close" refers to touching or near touching.

As used herein, the term "effective amount" refers to the amount of a composition (e.g., MIP) sufficient to accomplish beneficial or desired results. An effective amount can be administered and/or combined with another material in one or more administrations, applications or dosages and is not intended to be limited to a particular formulation or administration route.

As used herein, the term "animal" refers to any one or more species in the kingdom of animalia. This includes, but is not limited to livestock, other farm animals, domestic animals, pet animals, marine and freshwater animals, and wild animals.

As used herein, the term "feedstuffs" refers to material(s) that are consumed by a human or animal that contribute energy and/or nutrients to the subject. Examples of feedstuffs include, but are not limited to, dairy products, juices, grains, including but not limited to distillers grains, fruits, vegetables, meats, Total Mixed Ration (TMR), forage(s), pellet(s), concentrate(s) of any of the previous items, premix(es) or coproduct(s) of any of the previous products, molasses, fiber(s), fodder(s), grass(es), hay, kernel(s), leaves, meals made from any of the previous products, soluble(s) and supplement(s) containing any of the previous products.

As used herein, the term "mycotoxin" refers to toxic and/or carcinogenic compound(s) produced by various fungal species. In embodiments, the mycotoxin is an aflatoxin.

As used herein, the term "mycotoxicosis" refers to a condition in which mycotoxins pass the resistance barriers of a human or animal body. Mycotoxicosis can be considered either an infection or a disease and may have a deleterious effect on those afflicted.

As used herein, the term "toxic" refers to any detrimental, deleterious, harmful, or otherwise negative effect(s) on an animal or human, including, but not limited to a cell or a tissue of such animal or human. As used herein the terms "detrimental", "deleterious", "harmful", or "otherwise negative" with respect to "effect" can be determined by comparing the same cell or tissue of an animal or human prior to the contact or administration of a toxin or toxicant and after such contact and detecting an undesirable change in such cell or tissue when making such comparison.

As used herein, the term "traceability" refers to the property of the result of a measurement or the value of a standard whereby it can be related to stated references, usually national or international standards, through an unbroken chain of comparisons, all having stated uncertainties. It is the practical application of general metrology concepts to chemical measurements and provides the terminology, concepts and strategy for ensuring also that analytical chemical measurements are comparable. It measures the uniquely identifiable entities in a way that is verifiable. Traceability measures are utilized, among other things, to interrelate the chronology, location, and/or application of an item by means of documented recorded identification.

As used herein, the term "alkyl", by itself or as part of another substituent, refers to, unless otherwise stated, a straight or branched chain, or cyclic hydrocarbon radical, or combination thereof, which is fully saturated, having the number of carbon atoms designated (e.g., C1-C6 means one to six carbons). Examples of alkyl groups include, but are not limited to, methyl, ethyl, n-propyl, isopropyl, n-butyl, t-butyl, isobutyl, cyclohexyl, homologs and isomers of, for example, n-pentyl, n-hexyl, and the like.

As used herein, the term "heteroalkyl", by itself or as part of another substituent, refers to, unless otherwise stated, a straight or branched chain, or cyclic hydrocarbon radical, or combination thereof, which is fully saturated, having the number of carbon atoms designated (e.g., C1-C6 means one to six carbons) in which one of the carbon atom is replaced by a heteroatom. In embodiments a heteroatom is an oxygen.

As used herein, the term "substituted alkyl", unless otherwise stated, refers to a straight or branched chain, or cyclic hydrocarbon radical, or combination thereof, which is fully saturated, having the number of carbon atoms designated (e.g., C1-C6 means one to six carbons) and having a substitution of at least one of the H atoms. Examples of alkyl groups include methyl, ethyl, n-propyl, isopropyl, n-butyl, t-butyl, isobutyl, cyclohexyl, homologs and isomers of, for example, n-pentyl, n-hexyl, and the like.

Examples of substituents that can be used in a substituted alkyl include, but are not limited to, halogens, carboxy, and hydroxyl groups. As used herein, the term "halo substituted alkyl", by themselves or in combination with other terms, unless otherwise stated, refers to a substituted alkyl wherein a halo atom is used to replace at least one of the H atoms.

As used herein, the terms "cycloalkyl" and "heterocycloalkyl" by themselves or in combination with other terms, refer to, unless otherwise stated, cyclic versions of "alkyl"

and "heteroalkyl" respectively. Additionally, for heterocycloalkyl, a heteroatom can occupy the position at which the heterocycle is attached to the remainder of the molecule.

The terms "halo" or "halogen," by themselves or in combination with other terms, mean, unless otherwise stated, a fluorine, chlorine, bromine, or iodine atom. Additionally, terms such as "haloalkyl", are meant to include one or more substituted alkyl groups with halogen atoms that can be the same or different, in a number ranging from one to (2m+1), where m is the total number of carbon atoms in the alkyl group. Thus, the term "haloalkyl" includes monohaloalkyl (alkyl substituted with one halogen atom) and polyhaloalkyl (alkyl substituted with halogen atoms in a number ranging from two to (2m+1) halogen atoms).

The term "alkoxy," refers to one or more alkyl groups attached to the remainder of the molecule via an oxygen atom.

DETAILED DESCRIPTION

This disclosure describes aflatoxin template(s), compounds containing one or more such aflatoxin templates, and molecularly imprinted polymers made using such compounds, and methods of making and using such templates and compounds.

Aflatoxin Template(s) and Intermediates

In embodiments, aflatoxin templates described herein are structural analogs to aflatoxin molecules. In other embodiments, aflatoxin template(s) are similar in shape, size, charge density, geometry and/or other physical or chemical properties to one or more aflatoxins. In specific embodiments, an aflatoxin template comprises a coumarin moiety, at least one alkoxy moiety, and a carbonyl moiety. Aflatoxins molecules include one or more types of aflatoxin B1, B2, G1, G2, M1, M2, P1, and Q1.

In embodiments, Aflatoxin B1 (AFB1) was used as a model to create a structural analog using the synthesis described herein. Aflatoxin analogs are advantageous because they reduce or eliminate the need to handle large quantities of toxic aflatoxins and to prevent bleeding of aflatoxins out of the polymer. In embodiments, at least two different aflatoxin templates are prepared. In embodiments, aflatoxin templates have reduced or no toxicity as compared to naturally occurring aflatoxins.

An aflatoxin template has or comprises a Formula (I):

(I)

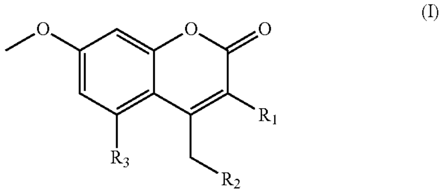

wherein $R_1$ is selected from H, $C_{1-6}$ alkyl, substituted $C_{1-6}$ alkyl, and a halo substituted $C_{1-6}$ alkyl; $R_2$ is selected from halo, $C_{1-6}$ alkyl, substituted $C_{1-6}$ alkyl, a halo substituted $C_{1-6}$ alkyl, $CH_2C(O)OR'$, and $CH(C(O)OR')_2$, R' is selected from H, $C_{1-6}$ alkyl, substituted $C_{1-6}$ alkyl, and a halo substituted $C_{1-6}$ alkyl; and $R_3$ is selected from H, $C_{1-6}$ alkoxy, and substituted $C_{1-6}$ alkyl. In related embodiments, R' is one or more substituents selected from a group consisting of halo, oxo, hydroxy and alkoxy.

In embodiments, $R_1$, $R_2$, $R_3$, and R' may independently be alkyl groups. An alkyl, refers to a straight or branched chain, or cyclic hydrocarbon radical, or combination thereof, which is fully saturated, having the number of carbon atoms designated (e.g., C1-C6 means one to six carbons). Examples of alkyl groups include methyl, ethyl, n-propyl, isopropyl, n-butyl, t-butyl, isobutyl, cyclohexyl, homologs and isomers of, for example, n-pentyl, n-hexyl, and the like.

In embodiments, $R_1$, $R_2$, $R_3$, and R' may independently be substituted alkyl groups. A substituted alkyl is a straight or branched chain, or cyclic hydrocarbon radical, or combination thereof, which is fully saturated, having the number of carbon atoms designated (e.g., C1-C6 means one to six carbons) and having a substitution of at least one of the H atoms. Examples of alkyl groups include methyl, ethyl, n-propyl, isopropyl, n-butyl, t-butyl, isobutyl, cyclohexyl, homologs and isomers of, for example, n-pentyl, n-hexyl, and the like. Examples of substitutions include halogens, carboxy, and hydroxyl groups.

In embodiments, $R_1$, $R_2$, $R_3$, and R' may independently be a halogen. A halo group or halogen, refers to a fluorine, chlorine, bromine, or iodine atom. Additionally, haloalkyl includes alkyl substituted with one or more halogen atoms, each of which can be the same or different, in a number ranging from one to (2m+1), where m is the total number of carbon atoms in the alkyl group. Examples include monohaloalkyl (alkyl substituted with one halogen atom) and polyhaloalkyl (alkyl substituted with halogen atoms in a number ranging from two to (2m+1) halogen atoms). In embodiments, the halogen is a chlorine or fluorine.

In embodiments, $R_3$ may independently be an alkoxy. An alkoxy refers to those alkyl groups attached to the remainder of the molecule via an oxygen atom. Examples include methoxy, ethoxy and the like.

In some example embodiments, an aflatoxin template has or comprises the Formula:

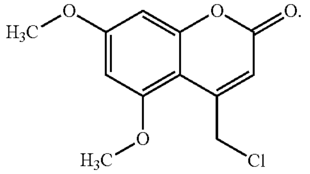 [SMILES: COc1cc(OC)c2c(CCl)cc(=O)oc2c1]

In a specific embodiment, an aflatoxin template is 4-(chloromethyl)-5,7-dimethoxy coumarin.

In other related embodiments, an aflatoxin template comprises an isolated molecule selected from the group consisting of

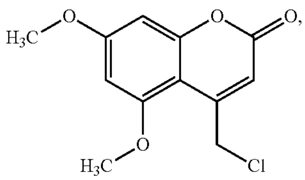

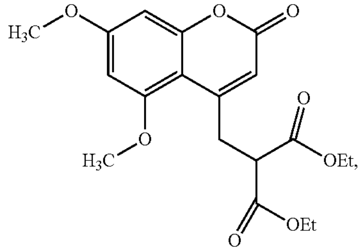

-continued

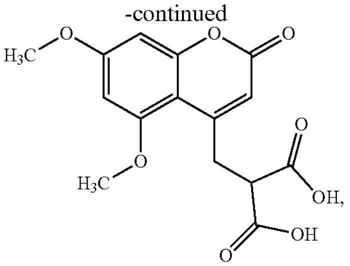

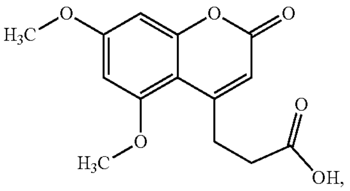

and combinations thereof.

In embodiments, an aflatoxin template comprises an isolated molecule selected from the group consisting of 2-((5,7-dimethoxy-2-oxo-2H-chromen-4yl)methyl) malonic acid, 3-(5,7-dimethoxy-2-oxo-2H-chromen-4yl)propanoic acid, propanedioic acid, 2-[(5,7-dimethoxy-2-oxo-2H-1-benzopyran-4-yl)methyl]-, 1,3-diethyl ester and combinations thereof.

In an alternative embodiment, an aflatoxin template has or comprises the Formula (I):

(I)

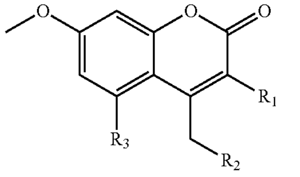

wherein $R_1$ together with $R_2$ form a $C_{4-7}$ cycloalkyl ring, a halo substituted $C_{4-7}$ cycloalkyl ring, an oxo substituted $C_{4-7}$ cycloalkyl ring, a $C_{4-7}$ cycloalkoxy ring, a hydroxy substituted $C_{4-7}$ cycloalkyl ring, or a carboxylic group substituted $C_{4-7}$ cycloalkyl; and $R_3$ is selected from H, $C_{1-6}$ alkoxy, and substituted $C_{1-6}$ alkyl.

In embodiments, cycloalkyl and heterocycloalkyl represent, cyclic versions of alkyl and heteroalkyl respectively. Additionally, for heterocycloalkyl, a heteroatom can occupy the position at which the heterocycle is attached to the remainder of the molecule.

In other related embodiments, an aflatoxin template has or comprises the Formula:

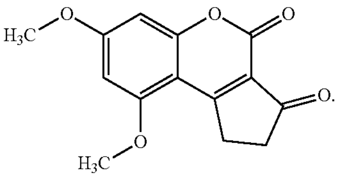 [SMILES: COc1cc(OC)c2c3c(c(=O)oc2c1)C(=O)CC3]

In a specific embodiment, the aflatoxin template is 5,7-dimethoxycyclo pentenon[2,3-c]coumarin.

Aflatoxin Template Synthesis

Aflatoxin templates and compounds containing such aflatoxin templates as described herein can be prepared by a variety of methods. The exemplary methods described herein provide processes (e.g., a synthetic process) and materials that allow large scale production of compounds containing one or more aflatoxin templates that are not only economical (e.g., that enables realizable, large scale production in an economically achievable manner), but that also use reagents that generally can be more readily available than reagents used to make mycotoxin templates previously.

In embodiments, a method of synthesis of an aflatoxin template of Formula (I) comprises reacting 3,5-dimethoxy phenol with ethyl 4-chloroacetoacetate in acid to form 4-(chloromethyl)-5,7-dimethoxy coumarin. In other embodiments, the compound 4-(chloromethyl)-5,7-dimethoxy coumarin is isolated and is used to form a MIP.

In embodiments, a method of synthesis of an aflatoxin template comprises suspending a monoacid according to the Formula of:

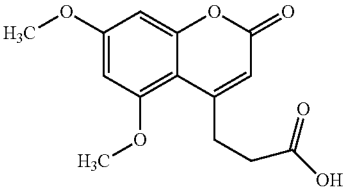 [SMILES: COc1cc(OC)c2c(CCC(=O)O)cc(=O)oc2c1]

in polyphosphoric acid and heating to at least 50° C.; cooling the reaction mixture below 50° C. and adding an aqueous to obtain an aflatoxin template according to the Formula of:

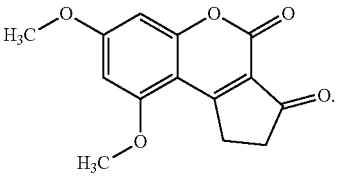 [SMILES: COc1cc(OC)c2c3c(c(=O)oc2c1)C(=O)CC3]

This aflatoxin template is isolated and used to form a MIP.

In embodiments, a method of providing a monoacid comprises suspending a diacid according to a Formula of:

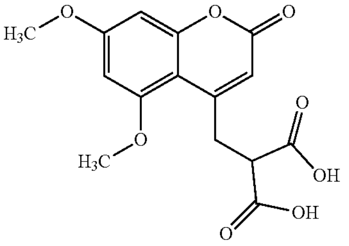 [SMILES: COc1cc(OC)c2c(CC(C(=O)O)C(=O)O)cc(=O)oc2c1]

in a solvent and heating to at least 100° C., or about 100 to 140° C.

In embodiments, a method of synthesis of an aflatoxin template comprises deprotecting a diester analog (i.e. propanedioic acid, 2-[(5,7-dimethoxy-2-oxo-2H-1-benzopyran-4-yl)methyl]-, 1,3-diethyl ester with a Formula of:

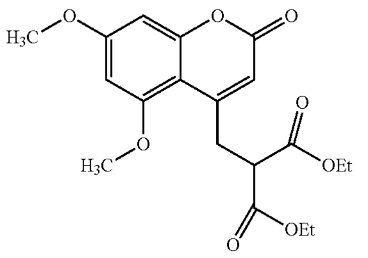 [SMILES: CCOC(=O)C(Cc1cc(=O)oc2cc(OC)cc(OC)c12)C(=O)OCC]

using a base (e.g. NaOH) in a solvent (e.g. ethanol) and heating to at least 60° C.; to form a diacid analog; and precipitating the diacid analog to isolate the aflatoxin template with the Formula of:

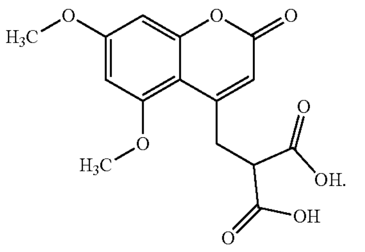 [SMILES: COc1cc(OC)c2c(CC(C(=O)O)C(=O)O)cc(=O)oc2c1]

In embodiments, a method of synthesis of diester intermediate (i.e., propanedioic acid, 2-[(5,7-dimethoxy-2-oxo-2H-1-benzopyran-4-yl)methyl]-, 1,3-diethyl ester) comprises combining 4-(chloromethyl)-5,7-dimethoxy coumarin with a Formula of:

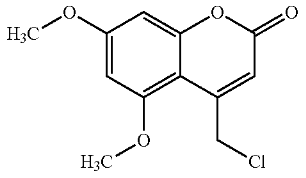 [SMILES: COc1cc(OC)c2c(CCl)cc(=O)oc2c1]

with diethyl malonate, potassium iodide, and a crown ether to form a diester analog; and precipitating the diester analog to isolate the aflatoxin template intermediate with the Formula of:

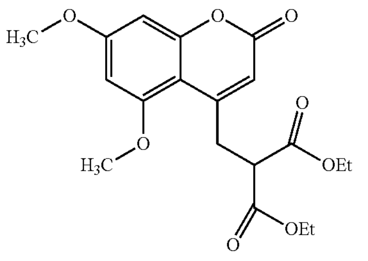 [SMILES: CCOC(=O)C(Cc1cc(=O)oc2cc(OC)cc(OC)c12)C(=O)OCC]

In embodiments, a method of synthesis of an aflatoxin template of Formula (I) comprises deprotecting propanedioic acid, 2-[(5,7-dimethoxy-2-oxo-2H-1-benzopyran-4-yl)methyl]-, 1,3-diethyl ester to form a diacid analog, and precipitating a diacid analog with the Formula of:

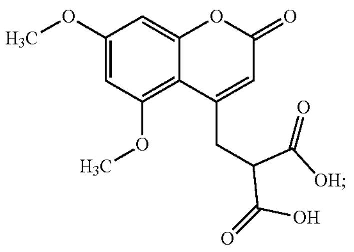 [SMILES: COc1cc(OC)c2c(CC(C(=O)O)C(=O)O)cc(=O)oc2c1]

suspending the diacid analog in a solvent and heating to 100° C., or 100 to 140° C. and precipitating a monoacid with the Formula of:

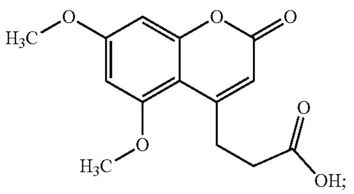 [SMILES: COc1cc(OC)c2c(CCC(=O)O)cc(=O)oc2c1]

suspending the monoacid in an acid and heating to at least 50° C., cooling the reaction mixture to below 50° C., and adding aqueous solution to obtain

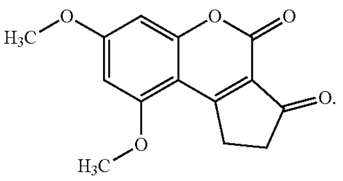 [SMILES: COc1cc(OC)c2c3c(c(=O)oc2c1)C(=O)CC3]

Figure 4:
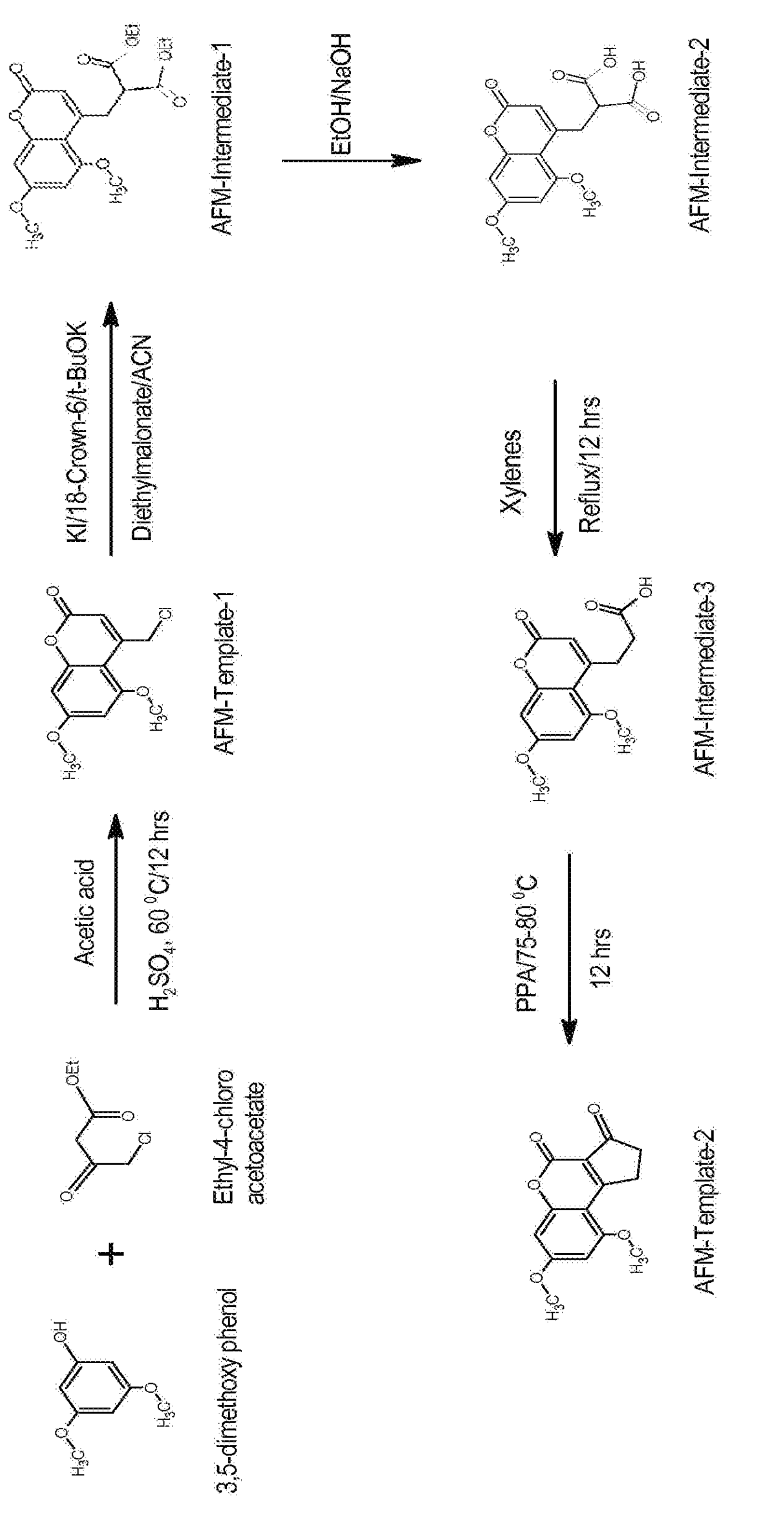
FIG. 4 is a schematic diagram of a synthesis of an aflatoxin template.

Referring now to FIG. 4 where aflatoxin template analogs and intermediate compounds were formed by condensation of 3,5-dimethoxyphenol with ethyl-4-chloroacetoacetate in presence of $H_2SO_4$ in toluene to form a chlorinated analog, 4-(chloromethyl)-5,7-dimethoxy coumarin. In this example, 4-(chloromethyl)-5,7-dimethoxy coumarin is combined with diethyl malonate, potassium iodide, and a crown ether in acetonitrile to form a mixture. Once the mixture is formed, potassium t-butoxide is added to the mixture to form a diester with the Formula propanedioic acid, 2-[(5,7-dimethoxy-2-oxo-2H-1-benzopyran-4-yl)methyl]-, 1,3-diethyl ester.

Upon the formation of the propanedioic acid, 2-[(5,7-dimethoxy-2-oxo-2H-1-benzopyran-4-yl)methyl]-, 1,3-diethyl ester, in this embodiment, a diacid is formed by deprotecting propanedioic acid, 2-[(5,7-dimethoxy-2-oxo-2H-1-benzopyran-4-yl)methyl]-, 1,3-diethyl ester using a base in alcohol. The diacid, having a Formula of:

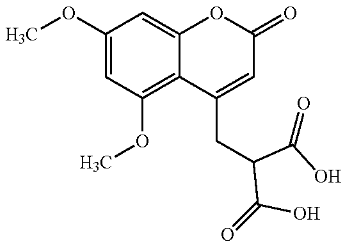 [SMILES: COc1cc(OC)c2c(CC(C(=O)O)C(=O)O)cc(=O)oc2c1]

is heated to at least 135° C. in a solvent. In this embodiment, the diacid is then converted to its monoacid by partial decarboxylation in xylene at reflux temperature. In at least this embodiment, the monoacid was subjected to cyclization using polyphosphoric acid to yield the final AFT-1 aflatoxin template (AFT-1) with the Formula of:

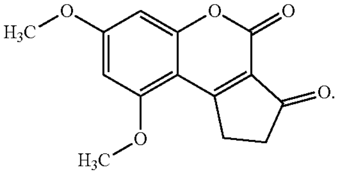 [SMILES: COc1cc(OC)c2c3c(c(=O)oc2c1)C(=O)CC3]

It should be appreciated that the chemical formula used, must allow for molecularly imprinted polymer intermediates, described in further detail below, to reversibly bind the aflatoxin template to the MIP. Additionally, the aflatoxin template contained in the aflatoxin template must provide a molecularly imprinted polymer intermediate with a cavity that retains a high level of affinity for one or more aflatoxins, such as aflatoxin B1.

In embodiments, a composition comprising an aflatoxin template and a carrier is provided. In embodiments, the composition includes an effective amount of the aflatoxin template to form a MIP with the desired characteristics (e.g. typically represented as an amount in relation to the amount of the monomer, a ratio). The compositions are formulated with suitable carriers, excipients, and other agents that provide suitable transfer, delivery, stability, and functionality of the aflatoxin template.

Molecularly Imprinted Polymers

In embodiments, a molecularly imprinted polymer comprises a crosslinked polymer comprising a monomer or made from a monomer, wherein the crosslinked polymer has a plurality of cavities, and at least one of the cavities is made with an aflatoxin template of Formula (I):

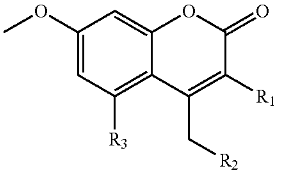

wherein $R_1$ is selected from H, $C_{1-6}$ alkyl, substituted $C_{1-6}$ alkyl, and a halo substituted $C_{1-6}$ alkyl; $R_2$ is selected from halo, $C_{1-6}$ alkyl, substituted $C_{1-6}$ alkyl, a halo substituted $C_{1-6}$ alkyl, $CH_2C(O)OR'$, and $CH(C(O)OR')_2$; wherein R' is selected from H, $C_{1-6}$ alkyl, and substituted $C_{1-6}$ alkyl; and $R_3$ is selected from H, $C_{1-6}$ alkoxy, and substituted $C_{1-6}$ alkyl; or wherein $R_1$ together with $R_2$ form a $C_{4-7}$ cycloalkyl ring, a halo substituted $C_{4-7}$ cycloalkyl ring, an oxo substituted $C_{4-7}$ cycloalkyl ring, a $C_{4-7}$ cycloalkoxy ring a hydroxy substituted $C_{4-7}$ cycloalkyl ring, or a carboxylic group substituted $C_{4-7}$ cycloalkyl; and $R_3$ is selected from H, $C_{1-6}$ alkoxy, and substituted $C_{1-6}$ alkyl.

In embodiments, at least one cavity provides for binding of the aflatoxin template of Formula (I). In an embodiment, a MIP selectively binds one or more aflatoxin templates. In embodiments, a MIP selectively binds one or more types of aflatoxins, for example, aflatoxins B1, B2, G1, G2, M1, M2, P1, and Q1. In embodiments, the affinity and/or selectivity of the MIP for an aflatoxin is compared to a corresponding NIP.

In some cases, all or a portion of the binding of the aflatoxin template or aflatoxin is reversible under certain conditions. After an MIP intermediate is formed, an aflatoxin template is removed using a solvent. In embodiments, a solvent is selected that can disrupt the interaction of the aflatoxin template with the polymer and has a similar polarity and/or solubility as the aflatoxin template. In embodiments, the solvent is a polar solvent.

Alternatively, after the MIP has bound aflatoxin from a material and is separated from the material, in embodiments, the bound aflatoxin can be removed in order to reuse the MIP. In embodiments, at least a portion of the bound aflatoxin and/or aflatoxin template is removable from the MIP using a solvent, such as a polar solvent. In embodiments, a solvent is selected that can disrupt the interaction of the aflatoxin with the polymer and has a similar polarity and/or solubility as the aflatoxin. In embodiments, a solvent is selected from the group of ethyl alcohol, methyl alcohol, acetonitrile, toluene, and a mixture of thereof. In some embodiments, about 25% or less of the aflatoxin bound to the MIP is released based on weight per volume in the presence of a solvent. In embodiments, the MIP releases 25%, 20%, 15%, 10%, 5%, or 1% or less by weight of one or more aflatoxins sequestered from a material, for example, in polar solvent. In contrast, about 90% or more aflatoxin is released from a corresponding NIP in the presence of the same solvent.

In embodiments, the MIP binds to the aflatoxin template with a chemical and/or physical interaction. In other embodiments, the polymer network forming the cavities binds to the aflatoxin template with a covalent or noncovalent bond. In embodiments, a MIP comprises micropores of about 20 Angstroms or less, and/or meso- and macropores between about 20 and 2000 Angstroms. In embodiments, an aflatoxin template has a molar volume of at least 300 cubic Angstroms. In other embodiments, the MIP has one or more cavities or pores that have a molar volume of at least 300 cubic Angstroms.

In embodiments, an aflatoxin template has a formula of Formula (I) as described herein. In a specific embodiment, the aflatoxin template of Formula (I) is selected from the group consisting of 4-(chloromethyl)-5,7-dimethoxy coumarin, 5,7-dimethoxycyclo pentenon[2,3-c]coumarin, and combinations thereof. In embodiments, a molecularly imprinted polymer is synthesized using more than one of the aflatoxin templates of Formula (I).

In embodiments, a polymer is formed from a monomer. A monomer is selected taking into account structural features of the aflatoxin template in order to assess which monomer or combination of monomers is most likely to form interactions (e.g., covalent, non-covalent, ionic, hydrogen bonds, hydrophobic interactions, van der Waals interactions) with the template. In the case of polymeric or oligomeric compounds that are to be utilized in vivo (e.g., as therapeutics or diagnostics, or as consumable sequestering components of animal feed or human foodstuffs), it is important to select monomers that are non-toxic and which exhibit suitable in vivo stability and solubility. Preferred examples for an aflatoxin MIP include, but are not limited to, acrylamides and methacrylates. Alternatively, the polymer may be treated post-polymerization to enhance the template solubility, e.g., by reaction with suitable organic or inorganic reagents.

Classes of monomers and specific monomers (e.g., utilized in MIP synthesis methods of the disclosure) include, but are not limited to, the following classes and derivatives thereof: acrylic acid and derivatives (e.g., 2-bromoacrylic acid, acryloyl chloride, N-acryloyl tyrosine, N-acryoyl pyrrolidinone, trans-2-(3-pyridyl)-acrylic acid), acrylates (e.g., alkyl acrylates, allyl acrylates, hydroxypropyl acrylate), methacrylic acid and derivatives (e.g., itaconic acid, 2-(trifluoromethyl) propenoic acid), methacrylates (e.g., methyl methacrylate, hydroxyethyl methacrylate, 2-hydroxyethyl methacrylate, 3-sulfopropyl methacrylate sodium salt, ethylene glycol monomethacrylate), styrenes (e.g., (2, 3 and 4)-aminostyrene, styrene-4-sulfonic acid, 3-nitrostyrene, 4-ethystyrene), vinyls (e.g., vinyl chloroformate, 4-vinylbenzoic acid, 4-vinylbenzaldehyde, vinyl imidazole, 4-vinylphenol, 4-vinylamine, acrolein), vinylpyridines (e.g., (2, 3, and/or 4)-vinylpyridine, 3-butene 1,2-diol), boronic acids (e.g., 4-vinylboronic acid), sulfonic acids (e.g., 4-vinylsulfonic acid, acrylamido-2-methyl-1-propane-sulphonic acid), metal chelators (e.g., styrene iminodiacetic acid), acrylamides and derivatives (e.g., N-methyl acrylamide), methacrylamides and derivatives (e.g., N,N-dimethyl acrylamide, N-(3-aminoprpoyl) methacrylamide), alkenes (e.g., 4-pentenoic acid, 3-chloro-1-phenyl-1-propene) (meth)acrylic acid anhydride and derivatives (e.g., methacrylic anhydride), silicon-containing monomers (e.g., (3-methacryloxypropyl) trimethoxy silane, tetramethyldisiloxane), polyenes (e.g., isoprene, 3-hydroxy-3,7,11-trimethyl-1,6,10-dodecatriene), azides (e.g., 4-azido-2,3,5,6-tetrafluorobenzoic acid), thiols (e.g., allyl mercaptan). Acrylate terminated or otherwise unsaturated urethanes, carbonates and epoxies can also be used in embodiments of the present invention, as can silicon-based monomers.

If utilized, one or more crosslinking agents will preferably be one or several polymeric or oligomeric compounds, or a compound that provides for cleavage under specific conditions. Crosslinking agents that lend rigidity to the subject polymeric compounds are known to those skilled in the art, and include, but are not limited to, di-, tri-, tetra- and penta-functional acrylates, methacrylates, acrylamides, vinyls, allyls, and styrenes. Specific examples of cross-linking agents include but are not limited to p-divinylbenzene, ethylene glycol dimethacrylate (abbreviated as EGDMA), tetramethylene dimethacrylate (abbreviated as TDMA), N,N'-methylene bisacrylamide (MDAA),N,N'-1,3-phenylenebis(2-methyl-2-propenamide)(PDBMP), 2,6-bisacryloylamidopyridine, 1,4-diacryloyl piperazine (abbreviated as DAP), 1,4-phenylene diacrylamide, and N,O-bisacryloyl-L-phenylalaninol. Examples of reversible, cleavable crosslinkers include, but are not limited to, N,N'-bis-(acryloyl) cystamine, N,N-diallyltartardiamide, N,N-(1,2-dihydroxyethylene) bisacrylamide, N1-((E)-1-(4-vinylphenyl) methylidene)-4-vinylanilene, allyl disulfide, and bis (2-methacryloyloxyethyl))disulfide. In preferred embodiments, ethylene glycol dimethacrylate is used as a cross-linking agent. Although the preferred cross-linking monomer is ethylene glycol dimethacrylate, embodiments of the present invention are not limited to this agent, and other cross-linking monomers may be used, such as, divinylbenzene and trimethylolpropane trimethacrylate (abbreviated as TRIM).

Any ratio of simple monomers to crosslinking agents can be used that provides a MIP structure of appropriate integrity, e.g., that can be used in the context of the final application (e.g., in food or feed products, in water intended for aquaculture use, in vivo, etc). Those skilled in the art can select suitable ratios of monomers to provide the desired structural integrity, which is intimately related to the nature and structure of the targeted molecule and to the nature and structure of the template used.

In embodiments, a MIP has a molar aflatoxin template to monomer ratio of about 100:1 to 1:100 (w/w). For example, ratios of aflatoxin template to monomer ratios of about 1:2 to 1:7 are utilized. In other embodiments, a MIP has a molar monomer to crosslinker ratio of about 1:4 to 1:10.

In embodiments, a MIP changes volume when contacted with a solvent. In embodiments, a MIP contacted with an aqueous solvent can adsorb up to 10 times more water than its weight. In other embodiments, an MIP is selected that, when placed in a solvent, the volume of the MIP increases about 75%, 50%, 40%, 30%, 20%, 10%, 5% or less than the volume of the MIP in a dried state. The solvent or the solvent mixture used as a medium for MIP synthesis also has an impact on the swelling properties of MIP and on the size of cavities and pores size and distribution within the tri-dimensional MIP network and the formation of micro-, meso-, macrospheres and agglomerates. In embodiments, one or more porogens may be employed in the synthesis of a MIP in order to alter the cavity size or swellability of the MIP. In certain embodiments, polar solvents such as acetonitrile are used as a solvent or co-solvent for MIP polymerization when an increase in MIP swelling and increase of MIP cavity size is desired. Alternatively, such solvents are avoided when an increase in MIP swelling and MIP cavity size is not desired (e.g., when MIP is intended for use as a chromatographic column where swelling may impede flow rate and disturb the elution of analytes and the ability of the HPLC instrument to perform). In embodiments, the swellability of the MIP is compared to a corresponding NIP.

In embodiments, the characteristics of an MIP is compared to a corresponding NIP. A corresponding NIP comprises the same crosslinked polymer as the MIP but is formed in the absence of an aflatoxin template.

In embodiments, a composition comprises a MIP and a carrier. In embodiments, the composition includes an effective amount of the MIP to sequester aflatoxin from a material. In embodiments, the effective amount is an amount that provides for the sequestering of at least 40% of the aflatoxin in the material based on weight per unit of material, and/or that reduces aflatoxin in the material to less than 0.5 parts per billion (ppb). The compositions are formulated with suitable carriers, excipients, and other agents that provide suitable transfer, delivery, stability, and functionality of the MIP.

Methods of Synthesis of MIP

In embodiments, methods of synthesis of MIPs are described. Different polymerization methods may be used including free radical, cationic, and anionic polymerization. Polymerization conditions are selected and provided herein that do not adversely affect the active conformation of the compound for which a complementary polymeric compound is to be produced. In particularly preferred embodiments, free radical precipitation polymerization methods are used.

The method of making an MIP generally comprises providing an aflatoxin template, such as is shown according to Formula (I),

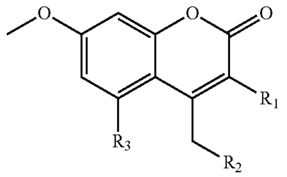

wherein $R_1$ is selected from H, $C_{1-6}$ alkyl, substituted $C_{1-6}$ alkyl, and a halo substituted $C_{1-6}$ alkyl; $R_2$ is selected from halo, $C_{1-6}$ alkyl, substituted $C_{1-6}$ alkyl, a halo substituted $C_{1-6}$ alkyl, $CH_2C(O)OR'$, and $CH(C(O)OR')_2$, R' is selected from H, $C_{1-6}$ alkyl, substituted $C_{1-6}$ alkyl, and a halo substituted $C_{1-6}$ alkyl; and $R_3$ is selected from H, $C_{1-6}$ alkoxy, and substituted $C_{1-6}$ alkyl; or wherein $R_1$ together with $R_2$ form a $C_{4-7}$ cycloalkyl ring, a halo substituted $C_{4-7}$ cycloalkyl ring, an oxo substituted $C_{4-7}$ cycloalkyl ring, a $C_{4-7}$ cycloalkoxy ring a hydroxy substituted $C_{4-7}$ cycloalkyl ring, or a carboxylic group substituted $C_{4-7}$ cycloalkyl; and $R_3$ is selected from H, $C_{1-6}$ alkoxy, and substituted $C_{1-6}$ alkyl; and combining the aflatoxin template with at least one monomer and one or more crosslinkers. Upon combining the monomer and crosslinker(s), the monomer and crosslinker(s) are polymerized to form a molecularly imprinted polymer intermediate.

A corresponding non-imprinted polymer (NIP) for a specific MIP is formed using the same method, same monomer, and same crosslinker as the MIP but lacks the presence of the aflatoxin template.

The disclosure also provides compositions comprising a MIP as described herein in a carrier. In embodiments, the carrier is a physiologically acceptable carrier. In other embodiments, the carrier is a solvent.

Molecularly Imprinted Polymer Intermediates

The aflatoxin template combined with a MIP precursor polymer forms a molecularly imprinted polymer intermediate. This molecularly imprinted polymer intermediate is a complex of a crosslinked MIP precursor polymer, having been made using a monomer, and an aflatoxin template. In at least one embodiment, the aflatoxin template has or comprises a compound of Formula (I):

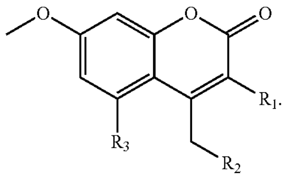

wherein $R_1$ is selected from H, $C_{1-6}$ alkyl, substituted $C_{1-6}$ alkyl, and a halo substituted $C_{1-6}$ alkyl; $R_2$ is selected from halo, $C_{1-6}$ alkyl, substituted $C_{1-6}$ alkyl, a halo substituted $C_{1-6}$ alkyl, $CH_2C(O)OR'$, and $CH(C(O)OR')_2$, R' is selected from H, $C_{1-6}$ alkyl, substituted $C_{1-6}$ alkyl, and a halo substituted $C_{1-6}$ alkyl; and $R_3$ is selected from H, $C_{1-6}$ alkoxy, and substituted $C_{1-6}$ alkyl; or wherein $R_1$ together with $R_2$ form a $C_{4-7}$ cycloalkyl ring, a halo substituted $C_{4-7}$ cycloalkyl ring, an oxo substituted $C_{4-7}$ cycloalkyl ring, a $C_{4-7}$ cycloalkoxy ring a hydroxy substituted $C_{4-7}$ cycloalkyl ring, or a carboxylic group substituted $C_{4-7}$ cycloalkyl; and $R_3$ is selected from H, $C_{1-6}$ alkoxy, and substituted $C_{1-6}$ alkyl. In particular, the aflatoxin template analog is selected from the group consisting of 4-(chloromethyl)-5,7-dimethoxy coumarin and 5,7-dimethoxycyclo pentenon[2,3-c] coumarin.

In some embodiments, the aflatoxin template and at least one monomer and one or more crosslinkers is combined in one or more organic solvents. In embodiments, one or more solvents are selected from the group consisting of acetonitrile, toluene, cyclohexane, polyvinyl alcohol in water solution, and a mixture of two or more of acetonitrile, toluene, cyclohexane, polyvinyl alcohol in water solution. In a specific embodiment, a mixture of acetonitrile and toluene is used as a solvent. In particular, the solution of acetonitrile and toluene comprises at least about 20% acetonitrile.

In other related embodiments, an initiator is used to generate free radicals formed by thermal decomposition. Initiating agents include but are not limited to azo-bisisobutyronitrile (abbreviated as AIBN), azo-bisdimethylvaleronitrile (abbreviated as ABDV), dimethylacetal of benzil, benzoylperoxide (abbreviated as BPO), and 4,4'-azo(4-cyanovaleric acid). In a specific embodiment, azo(bis)-isobutyronitrile is the initiator. In embodiments, polymerization is initiated by forming free radicals in an organic solvent at a temperature between 55 and 110° C.

In embodiments, a method of synthesis further comprises adding a porogen to change the size of the cavities and the swellability of the MIP. Examples of porogens include toluene, xylene, and ethylbenzene.

The molecularly imprinted polymer intermediate can be made using an aflatoxin template compound to monomer ratio from about 100:1 to 1:100. In other embodiments an aflatoxin template compound to monomer ratio is from about 1:2 to 1:7.

The molecularly imprinted polymer intermediate can also be made using a crosslinker, and the monomer to crosslinker ratio can be from about 1:4.1 to 1:10.

Table 1 provides a series of examples of molecularly imprinted polymer (MIP) intermediates and non-imprinted polymer (NIP) intermediates and several aflatoxin template to monomer ratios and monomer to crosslinker ratios that are within the scope of the molecularly imprinted polymer intermediates described herein.

TABLE 1

Ratios of template vs. monomer vs crosslinker for the preparation of 6 MIPs and NIPs.

| Product Name | Mole Ratio Template:Monomer | Mole Ratio Monomer:Crosslinker | Synthesis Yield | Mass (g) |
|---|---|---|---|---|
| MIP-001 | 1:2.0 | 1:5.7 | 50.2% | 1.36 |
| NIP-001 | — | 1:5.8 | 91.3% | 4.93 |
| MIP-002 | 1:2.3 | 1:9.6 | 76.3% | 3.50 |
| NIP-002 | — | 1:9.2 | 89.4% | 4.14 |
| MIP-003 | 1:4.6 | 1:4.1 | 62.1% | 3.03 |
| NIP-003 | — | Not Synthesized | N/A | 0.00 |
| MIP-004 | 1:4.0 | 1:10.0 | 74.7% | 6.22 |
| NIP-004 | — | 1:10 | 93.4% | 7.78 |
| MIP-005 | 1:6.8 | 1:5.8 | 117.3% | 13.54 |
| NIP-005 | — | 1:5.8 | 98.0% | 11.31 |
| MIP-006 | 1:7.1 | 1:9.6 | 69.3% | 7.19 |
| NIP-006 | — | 1:9.4 | 57.7% | 5.33 |

Once the molecularly imprinted polymer intermediate is formed, it is precipitated and the aflatoxin template is removed from the molecularly imprinted polymer intermediate to form a molecularly imprinted polymer. This process can be achieved by washing the molecularly imprinted polymer intermediate with a solvent. In embodiments, a solvent is selected that has a similar polarity and/or solubility as the aflatoxin template. In embodiments, an organic solvent is selected from the group of ethyl alcohol, methyl alcohol, acetonitrile, toluene, and a mixture of thereof. Aflatoxin template removal can be determined by known methods such as by LC-MS. Upon removal of the aflatoxin template, a molecularly imprinted polymer is formed and available to sequester an aflatoxin molecule. In embodiments, the MIP is dried.

In embodiments, yield of the MIP can be enhanced by increasing the template to monomer ratio and/or increasing the monomer to crosslinker ratio. In embodiments, the template to monomer ratio is at least 1:2 and/or the monomer to crosslinker ratio of at least 1:6.

Method of Use

The disclosure provides methods of sequestering one or more aflatoxins comprising contacting a molecularly imprinted polymer comprising a crosslinked polymer having a plurality of cavities, wherein at least some of the cavities provides for reversible binding to at least one of the aforementioned aflatoxins. Once the MIP is formed, it can be placed within or on a material suspected of containing an aflatoxin, optionally containing an aflatoxin, or known to contain an aflatoxin. It should be appreciated that the materials containing aflatoxin could be a gas, semi-gas, liquid, semi-liquid, or solid. In exemplary embodiments, the materials containing aflatoxin are selected from the group consisting of soil, a spice, a beverage, a foodstuff, an animal feed, a pharmaceutical composition, a nutraceutical composition, and a cosmetic composition. In one embodiment, the material containing aflatoxin is milk.

A select amount (e.g. effective amount, or inclusion rate) of MIP is exposed to the material containing or suspected of containing aflatoxin. In embodiments, an amount of the MIP per unit of material is at least 0.01%. For example, an MIP synthesized with a molar aflatoxin template compound to monomer ratio of at least 1:6.8, a molar monomer to crosslinker ratio of at least 1:5.8, and has an inclusion rate of at least 0.1%, adsorbs at least 76.5% of the aflatoxin M1(AFM1) from a 100 ng/L AFM1 solution in buffer. In another example, an inclusion rate of at least 1.0% showed 100% adsorption of AFM1. In other embodiments, the MIP/material ratio is at least 0.01% to 100%. In embodiments, an amount of MIP per volume of liquid is about 100 mg to 1 kilogram per liter of material.

In embodiments, a MIP is contacted with the material containing or suspected of containing aflatoxin for at least 1 second. In other embodiments, the MIP is contacted with the material containing aflatoxin or suspected of containing aflatoxin for about 1, 2, 3, 4, 5 minutes or more. In other embodiments, the MIP is contacted with the material from about 1 second to 500 minutes.

In embodiments, the material and the MIP are contacted in a solution with a pH of 1-13. In other embodiments, the pH is about pH 6.0, pH 7.0, pH 7.5, or less.

In embodiments, the MIP is contacted with the material in batch with or without agitation. In other embodiments, an MIP is placed in a chromatography column, such as solid phase extraction column.

Once the MIP is in contact with the material for a predetermined period of time, the MIP, which now contains sequestered aflatoxin, is separated from the material. One such separation method is filtration. Another separation method is centrifugation.

Adsorption of the aflatoxin by the MIP ranges from at least 10%, 20%, 30, or 40% or greater of the weight of an aflatoxin per unit of material. Adsorption obtained from a material is specific to the conditions used in terms of pH, temperature, concentration of toxin, nature of MIP, agitation, and flow of the material. If time of exposure of the MIP to the mycotoxin is increased and/or the inclusion rate is increased, then a 100% adsorption is observed. Adsorption is affected by time of exposure, concentration of aflatoxin, inclusion level of the MIP, and environment. When the material is exposed to the MIP for at least 5 minutes, with an inclusion rate of at least 0.1%, the MIP can sequester at least 40% by weight of the aflatoxin in the material. In related embodiments, the MIP will sequester a sufficient amount of aflatoxin from the material to reduce the amount of aflatoxin in the material to less than 0.5 or less than 0.05 parts per billion.

In some embodiments, the material can be contacted with a MIP for multiple exposures until aflatoxin levels are reduced. For example, a first exposure of the material to a MIP can remove about 10% or more of the aflatoxin. The MIP with bound aflatoxin is then removed and washed and reused or MIP with little or no bound aflatoxin is then contacted with the material again. Multiple exposures can continue until the amount of aflatoxin is reduced for example, to less than 0.5 ppb.

Optionally, after separation of MIP with bound aflatoxin, aflatoxin can be removed from the MIP by treating with a solvent that can disrupt the chemical association of the aflatoxin with the MIP. However, there is a balance between affinity of the MIP for binding of the aflatoxin and the amount of bound aflatoxin that can be removed. In embodiments, for a MIP with high affinity for aflatoxin, the MIP releases about 25%, 20%, 15%, 10%, 5%, 1% or less of the aflatoxin sequestered from the material in the presence of a solvent, for example, as compared to a corresponding NIP. In certain embodiments, it is desirable to reuse a MIP from which aflatoxin previously sequestered has been removed beforehand according to suitable and sufficient amount of organic solvent washes so that no detectable amount of aflatoxin can be found leaching from the MIP material using conventional LC-UV or LC-fluorescence, or LC-MS quantitative methodologies.

Another optional step in the process of using MIPs for the sequestering of aflatoxin, is to detect the amount of aflatoxin (i.e. parts per billion (ppb)) in a material prior to treatment with an MIP. Additionally, the material may be again tested, during and/or after treatment with an MIP to determine sequester rate of the aflatoxin. Furthermore, the amount of MIP required to sequester a pre-determined concentration of aflatoxin may also be elucidated, depending on the particular MIP utilized. Moreover, the MIP complexed with aflatoxin, once separated from the material, may be tested for aflatoxin concentration sequestered.

Quantitative adsorption efficacy can be determined by using UPLC-Xevo-TQD MS/MS (Waters Corp.). For example, a gradient of water/0.1% formic acid (v/v) and methanol/0.1% methanol (v/v) is used and analytes can be separated on an Acquity UPLC® BEH C18 1.7 μm 2.1×50 mm column (Waters. Corp.). The method is optimized for the analysis of AFM1/AFB1/aflatoxin template in buffer and milk using a C13-AFB1 isotopic dilution and normalization technique.

EXAMPLES

Synthesis of Aflatoxin M1 Template Molecules

Example 1 Preparation of 4-(chloromethyl)-5,7-dimethoxy Coumarin (AFM-Template-1)

Cold solution of ethyl-4-chloroacetoacetate (26.6 gr) in acetic acid (12.5 ml), and concentrated sulfuric acid (6.25 ml) was added drop-wise for 15 minutes to a solution of 3,5-dimethoxyphenol (25.0 gr) in acetic acid (50.0 ml) at 8-10° C. under nitrogen atmosphere. The reaction mixture was consecutively stirred at 20-25° C. for 1 hour, slowly heated to 60° C. and stirred for 12 hours at 55-60° C. The reaction mixture was cooled to 40° C. and hot water (150.0 ml) was added drop-wise over a period of 30 minutes at 40-45° C. The mixture was cooled to room temperature and stirred for 1 hour to precipitate the product. The product was filtered, washed with water (2×25 ml) and dried under suction for 30 minutes. Cold methanol (50.0 ml) was added to the crude product and the slurry was stirred at 8-10° C. for 30 minutes. The product was filtered and washed with cold methanol (2×25 ml) and dried under vacuum to obtain the final product, 4-(chloromethyl)-5,7-dimethoxy coumarin (AFM-Template-1), which had the appearance of a white fluffy powder (39 gr). The resulting product was carried forth and used in the next step as is.

Example 2 Preparation of 4-(2,2-dicarboethoxy-ethyl)-5,7-dimethoxycoumarin (AFM-Intermediate-1)

Diethylmalonate (32.75 gr) was added to a mixture of 4-(chloromethyl)-5,7-dimethoxy coumarin (AFM-Template-1, 40.0 gr), 18-Crown-6 (4.96 gr), and potassium iodide (3.12 gr) in acetonitrile (400 ml) at room temperature under nitrogen atmosphere. Potassium-t-butoxide (t-BuOK, 22.8 gr) was added in one lot to the reaction mixture (slightly exothermic) at room temperature. The temperature of the reaction mixture (suspension) was slowly increased to 40° C., and then stirred for 24 hours at 35-40° C. under nitrogen atmosphere. The reaction mixture was cooled to room temperature and evaporated to dryness under vacuum at 35-40° C. to produce a yellow semi-solid residue. The residue was dissolved in a mixture of water (200 ml) and ethylacetate (400 ml) under stirring. The pH of the mixture was adjusted to 5 with diluted hydrochloric acid. The organic layer was separated from the aqueous layer, this latter being further extracted with ethylacetate (2×200 ml). Organic layer dried over anhydrous sodium sulfate (100 gr) were combined and filtered. The filtrate was concentrated to dryness under vacuum at 35-40° C. to give the propanedioic acid, 2-[(5,7-dimethoxy-2-oxo-2H-1-benzopyran-4-yl) methyl]-, 1,3-diethyl ester (AFM-Intermediate-1), which had the appearance of a yellow solid (58 gr). The resulting product was carried forth and used in the next step as is.

Example 3 Preparation of Diacid (AFM-Intermediate-2)

Sodium hydroxide pellets (15.6 g) were added to a suspension of 4-(2,2-dicarboethoxy-ethyl)-5,7-dimethoxy-coumarin (AFM-Intermediate-1, 58.0 g) in ethyl alcohol (290 ml) at room temperature. The temperature of the reaction mixture (suspension) was slowly increased to 60° C., and then stirred for 3 hours at 60-65° C. The reaction mixture was cooled to room temperature and then pH of the mixture adjusted to 2 with concentrated hydrochloric acid to precipitate the product. The slurry was cooled to a temperature of 10° C. and stirred for 1 hour at 8-10° C. to complete precipitation of the product. The product was filtered (Crop-1), and then ethanol distilled-off from the mother liquor by distilling at 20-25° C. under vacuum, and then the concentrated mass was cooled to 10° C. to precipitate the product, filtered the same (Crop-2). The combined product was washed with 1:1 (v/v) mixture of methanol and water (2×200 ml) and then further dried under vacuum to obtain the diacid (AFM-Intermediate-2), which had the appearance of a yellow solid (45 g). The resulting product was carried forth and used in the next step as is.

Example 4 Preparation of Monoacid (AFM-Intermediate-3)

The diacid (AFM-Intermediate-2, 30 g) was suspended in m-xylene (300 ml) at room temperature. The temperature of the reaction mixture (suspension) was slowly increased to 135° C., and then stirred for 12 hours at 135-140° C. The reaction mixture was cooled down to room temperature and then the formed precipitated filtered. The precipitate was washed with n-Hexanes (2×100 ml) and dried under vacuum to obtain the monoacid (AFM-Intermediate-3), which appeared as half-white solid (25 g). The resulting product was carried forth and used in the next step as is.

Example 5 Preparation of 5,7-dimethoxycyclo Pentenon[2,3-c]coumarin (AFM-Template-2)

The monoacid (AFM-Intermediate-3, 4.75 g) was suspended in polyphosphoric acid (9.50 gr) at room temperature under nitrogen atmosphere. The temperature of the reaction mixture (suspension) was slowly increased to 75° C., and then stirred for 12 hours at 70-75° C. The reaction mixture was cooled to room temperature and then water (50 ml) was added slowly to decompose the excess polyphosphoric acid and the reaction mixture was stirred for 1 hour at room temperature. Dichloromethane (50 ml) was added to the reaction mixture and stirred for 15 minutes, organic layer was separated. The product was extracted with dichloromethane (2×25 ml). The combined organic layer was dried over anhydrous sodium sulfate (25 g) and concentrated to dryness by distillation under vacuum. The residue was suspended in methanol and stirred for 30 minutes at room temperature. The product was filtered and washed with methanol (2×10 ml) and then dried under vacuum to obtain 5,7-dimethoxycyclo pentenon[2,3-c]coumarin (AFM-Template-2), which appeared as half-white solid (2.5 g).

Example 6 Produced MIP Composition and Characteristics

Experiments were conducted during development of embodiments of the disclosure to test MIP polymers under their free flowing powder form for their adsorption properties toward AFM1 (Biopure, Romer Labs® Inc, Union, Mo.) mycotoxin and for the removal of the AFM1 mycotoxin from liquid or semi-liquid media via chemical interactions. The MIP produced was used herein to depict the differences in affinity of sequestration of the AFM1 mycotoxin and to evaluate the specificity of the material.

Six independent MIPs were prepared using AFT-1 (1.0 mmol, template), methacrylic acid (2.0 mmol, MAA, monomer), and ethylene glycol dimethacrylate (5.0 mmol, EGDMA, cross-linker) in a mixture of acetonitrile and toluene (1:3 v/v) at room temperature under nitrogen atmosphere by using different molar ratio of AFT-1 vs. MAA and monomer vs. cross-linker (Table 1). The solution was stirred for 1 h at RT under inert atmosphere. Then, the azo(bis)-isobutyronitrile (0.01 mmol, AIBN, initiator) was added and slowly heated and maintained for 30 min at 60-65° C. to precipitate the MIP microspheres. Two independent Non-Imprinted Polymers (NIP's) were also prepared through the same procedure but in the absence of AFT-1. The template (AFT-1) was removed from the MIP by continuous washing with toluene until complete disappearance of template in the washings as determined by the analysis of eluent through LC-UV, LC-fluorescence.

The resulting MIP and NIP polymeric material was synthesized as a block polymer which was ground to a powder with a mortar and pestle. The NIP polymeric material was white in color and when ground to a powder was highly electrostatic. The MIP polymeric materials were brown in color due to the presence of the brown colored template with the exception of MIP-005 which was red in color (a different synthesis batch template was used for this MIP which was red in color). Minimal color change was experienced during the toluene rinses of the MIP products. However when washed with methanol, the color of the powder was extremely muted and less dark as the colored template was rinsed from the polymer structure. The MIP polymeric materials in the powder form were also somewhat electrostatic, although not to the degree of the NIP products.

Swelling properties of powder forms of MIP/NIP were investigated (Table 2). We concluded that the swelling properties of MIP were considerably higher than NIPs. MIP-001 exhibited the greatest volume increase by swelling to 240% of its original size in buffer. MIP-002 also showed significant size increase to 200% of its original size. MIP-005 and NIP-005 were the only polymeric materials which showed no size increase when exposed to buffer for an extended period of time while NIP-004 showed a minimal 11% volume increase. The remaining MIP products all exhibited a moderate degree of volume increase due to swelling, to 150-167% of their original size.

TABLE 1

Ration of template vs. monomer vs cross linker for the preparation of 6 MIPs and Nips.

| Product Name | Mole Ratio Template:Monomer | Mole Ratio Monomer:Cross-linker | Synthesis Yield | Mass (g) |
|---|---|---|---|---|
| MIP-001 | 1:2.0 | 1:5.7 | 50.2% | 1.36 |
| NIP-001 | — | 1:5.8 | 91.3% | 4.93 |
| MIP-002 | 1:2.3 | 1:9.6 | 76.3% | 3.50 |
| NIP-002 | — | 1:9.2 | 89.4% | 4.14 |
| MIP-003 | 1:4.6 | 1:4.1 | 62.1% | 3.03 |
| NIP-003 | — | Not Synthesized | N/A | 0.00 |
| MIP-004 | 1:4.0 | 1:10.0 | 74.7% | 6.22 |
| NIP-004 | — | 1:10 | 93.4% | 7.78 |
| MIP-005 | 1:6.8 | 1:5.8 | 117.3% | 13.54 |
| NIP-005 | — | 1:5.8 | 98.0% | 11.31 |
| MIP-006 | 1:7.1 | 1:9.6 | 69.3% | 7.19 |
| NIP-006 | — | 1:9.4 | 57.7% | 5.33 |

TABLE 2

Percent volume expansion of each MIP/NIP powder after 90 h exposure to pH 6.0 ammonium acetate buffer solution in NMR tubes.

| Product | Percent Volume Increase |
|---|---|
| MIP-001 | 140% |
| MIP-002 | 100% |
| MIP-003 | 67% |
| MIP-004 | 50% |
| MIP-005 | 0% |
| MIP-006 | 67% |
| NIP-004 | 11% |
| NIP-005 | 0% |

Example 7 Produced MIP Sequestration Capabilities Toward Mycotoxins—Applied to AFM1 in Buffer Quantitative adsorption efficacy was carried out using UPLC-Xevo-TQD MS/MS (a.k.a., UPLC-MS/MS) (Waters Corp.). A gradient of water/0.1% formic acid (v/v) and methanol/0.1% methanol (v/v) was used and analytes were separated on an Acquity UPLC® BEH C18 1.7 μm 2.1×50 mm column (Waters. Corp.). The method was optimized for the analysis of AFM1/AFB1/AFT-1 in buffer and milk using a C13-AFB1 isotopic dilution and normalization technique.

Instant Trapping Properties

Experiments were conducted during development of embodiments of the disclosure to test for the inclusion rate of the MIP/NIP investigated by ramping said levels of inclusion from 0.001 to 1.0% (w/v) of material in a pH 6.0 environment. Several instant trapping studies were done to ascertain the viability of using MIP products to adsorb AFM1. To perform this study, 0.01 mg, 0.1 mg, 1.0 mg, and 10.0 mg of MIP-005 were loaded into extraction cartridges with polytetrafluoroethylene (PTFE) frits using a slurry technique in buffer for the lowest inclusion rates. Briefly, MIP was put in suspension using buffer and loaded onto the cartridge and weighted to determine the precise amount of the MIP. The quantities of MIP used in this experiment represent inclusion rates of 0.001%, 0.01%, 0.1%, and 1.0% (w/v). This experiment was performed at room temperature.

The polymeric material was "primed" by adding and subsequently eluting 1 volume (1 mL) of water, 1 of methanol, and 2 of buffer in succession. One milliliter of a solution of buffer spiked with 100 ng/L of AFM1 was then added to each cartridge and followed after 1 min by 1 mL of buffer with no AFM1. These final two elutions were collected in the same silanized UPLC vial for analysis of AFM1 content. A volume of 1 mL of methanol was added to the cartridges for the elution of trapped AFM1 and the eluent was collected followed by 1 mL of toluene eluent which was likewise collected separately for analysis. Methanol and toluene eluent samples were dried using nitrogen gas and reconstituted in 1 mL of buffer before analysis. To allow for effective quantification of results using the UPLC-MS/MS, standards were created of known concentrations of AFM1 in buffer at 1, 5, 10, 50, and 100 ng/L.

Results showed that 1 mg/L of free flowing polymer was sufficient for the adsorption of 76.5% toward 100 ng/L of AFM1, which was selected as potential aflatoxin target. FIG. 1. This inclusion rate was used as a reference for the rest of the MIP evaluation. Instant sorption of 100 ng/L of AFM1 by MIP and NIP packed into solid-phase extraction (SPE) cartridges and eluted with a 100% methanol solution was investigated. We found that the adsorption varied between 75.2 and 94.4 ng/L of AFM1 adsorbed.

The quantity of AFM1 present in the methanol and toluene extraction rinses serves as an indicator of the strength with which the AFM1 is being held by the MIP/NIP. We are demonstrating that each product tested released between 31.1 and 44.4 ng/L of AFM1 when washed with 100% methanol with two exceptions. MIP-001 released 64.3 ng/L of AFM1 and MIP-005 released a low 22.6 ng/L of AFM1.

However, with the exception of these two products, each of the MIPs and NIPs exhibited a similar degree of interaction strength with the AFM1. Little to no AFM1 was found in the toluene rinses for each of the MIP/NIP products. This is likely due to the fact that much of the AFM1 was released in the methanol extraction and also that the nonpolar nature of toluene had little effect on desorption of the polar AFM1. See FIG. 1.

Kinetic of Adsorption

Experiments were conducted during development of embodiments of the disclosure to test the time of reaction and its effect on the adsorption using free flowing MIP/NIP reacted under 225 rpm orbital shaking at pH 6.0 over 6 periods of time, from 5 to 500 minutes with a 90 ng/L AFM1 10 mL solution. Adsorption efficacy was measured by quantitation of the mycotoxin remaining in the supernatant and eluting from the MIP/NIP after methanol wash, which defined adsorption efficacy and selectivity. Due to the fact that there is instant adsorption, the AFM1 adsorption quantities for each time point (15, 30, 60, 90 minutes and 18 hrs) were averaged for each product. All test tubes were then centrifuged for 10 minutes at 3,000 rpm and a transferred into UPLC vial for analysis. The powder (MIP or NIP) was then transferred to a 2 mL Eppendorf tube where 1 mL of methanol was added and vortexed for approximately three seconds. Each tube was then centrifuged for 5 minutes at 10,000 rpm and 500 μL of liquid was removed and placed in a UPLC vial. The samples were then dried using nitrogen and reconstituted in 500 μL of buffer before analysis by means of a UPLC-MS/MS system.

Figure 2:
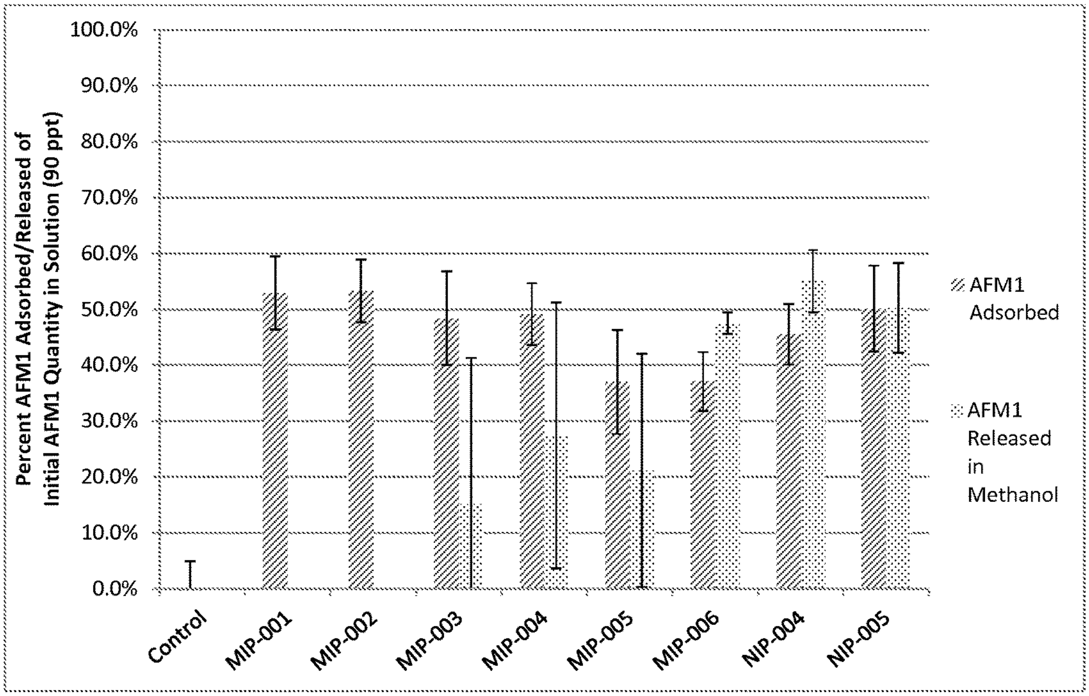
FIG. 2 shows average AFM1 adsorption averaged over multiple time points for the indicated MIPs and corresponding non-imprinted polymers (NIPs) (varying from 0.001%-0.1%)sing free flowing MIP/NIP over 6 periods of time, from 5 to 500 minutes with a 90 ng/L AFM1 10 mL solution. Adsorption efficacy was measured by quantitation of the mycotoxin remaining in the supernatant (▒) and eluting from the MIP/NIP after methanol wash (░), which defined adsorption efficacy and selectivity. Due to the fact that there is instant adsorption, the AFM1 adsorption quantities for each time point (15, 30, 60, 90 minutes and 18 hrs) were averaged for each product. All test tubes were then centrifuged for 10 minutes at 3,000 rpm and a transferred into UPLC vial for analysis. The powder (MIP or NIP) was then transferred to a 2 mL Eppendorf tube where 1 mL of methanol was added and vortexed for approximately three seconds.

All polymers at every time point were able to adsorb between 45 and 55% of AFM1 and non-significant differences were observed between MIP and NIP. See FIG. 2. Selectivity was however vastly different between MIP and NIP. MIPs depending on their formulation were only partially releasing AFM1. The differences observed in terms of release of the targeted molecule following methanol wash with the previous experiment, clearly demonstrated that the increase of the time of reaction between target molecule and MIP increased the stability of the sequestering, whereas NIP showed a lower stability of interaction resulting in the release of more of the targeted compound in the methanol wash. This experiment established the clear specificity of the interaction and adsorption quality of the MIP toward aflatoxin M1. Further investigation demonstrated that when different concentration of AFM1 were tested varying from 45 to 450 ng/mL, MIP/NIP exhibited similar adsorption capacity around 50%, accounting for a chemical equilibrium between adsorbed vs. non-adsorbed AFM1 present in the environment.

Example 8 Produced MIP Sequestration Capabilities Toward Mycotoxins—Applied to AFM1 in Milk Experiments were conducted during development of embodiments of the invention to test the MIP (MIP-003 for its capacity at interacting with 225 ng/L AFM1 in raw milk. A slurry of MIP-003 in LC-MS grade water was used to place 0.1 mg, 1.0 mg, and 10.0 mg of powder in respective silanized test tubes (1 mL of water from the slurry in each test tube). 1 mL of water was placed in two additional test tubes with no powder to serve as controls in the form of both spiked and blank raw milk. 9 mL of raw milk spiked to 250 ng/L AFM1 was then placed in each test tube, except for the blank milk control which received 9 mL of milk which was not spiked. All test tubes were then placed on an orbital shaker set to 200 rpm for one hour at room temperature following which the test tubes were centrifuged at 4,000 rpm for 10 minutes. Fourteen 100 mg C18 SPE cartridges (triplicate for each spiked milk sample and duplicate for the blank milk) were activated by eluting 1 mL of methanol and 1 mL of water in succession using vacuum pressure. After centrifugation, 1 mL of liquid was placed in each respective SPE cartridge and each sample, with the exception of the blank milk, was spiked with 10 μL of a 100 ppb sample of AFB1 in acetonitrile to serve as an internal standard. The liquids were then eluted using vacuum pressure followed by the elution of 1 mL of water through each cartridge. Following this, 1 mL of methanol was placed in each cartridge and eluted into a silanized UPLC vial using positive pressure. After elution, one of the two blank milk samples was spiked to 225 ng/L AFM1 and with 10 μL of the 100 ppb AFB1 internal standard solution. To allow for quantification of results, standards of 1, 5, 10, 25, 50, 100, 250, and 500 ng/L AFM1 concentration were created in acetonitrile. One milliliter of each sample was dried by blowing nitrogen over it and reconstituted in 1 mL of buffer. A volume of 500 μL of each standard was then spiked with 5 μL of the 100 ppb AFB1 solution to allow for the creation of a calibration curve.

Figure 3:
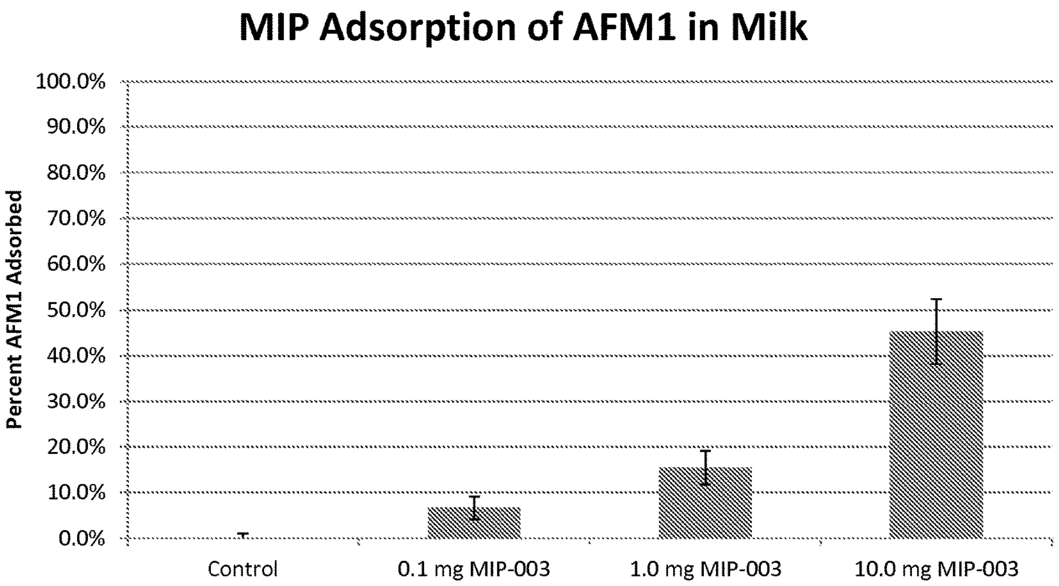
FIG. 3 shows average AFM1 adsorption averaged for MIP-003 (varying from 0.001%-0.1%) in 10 mL of raw milk spiked with a concentration of 225 ng/L AFM1.

At an inclusion rate of 0.1% (w/v), the MIP was able to remove 45.3% of the toxin. As seen in FIG. 3, we established that even 0.1 mg (0.001% inclusion rate) and 1.0 mg (0.01%) of free flowing powder also exhibited adsorption in the range of 6.7% and 15.4% of AFM1 removed from milk, respectively. This experiment clearly defined the applicability of MIP at targeting specifically AFM1 in a complex raw milk matrix even at inclusion rates as small as 0.001%.

Example 9

Figure 5:
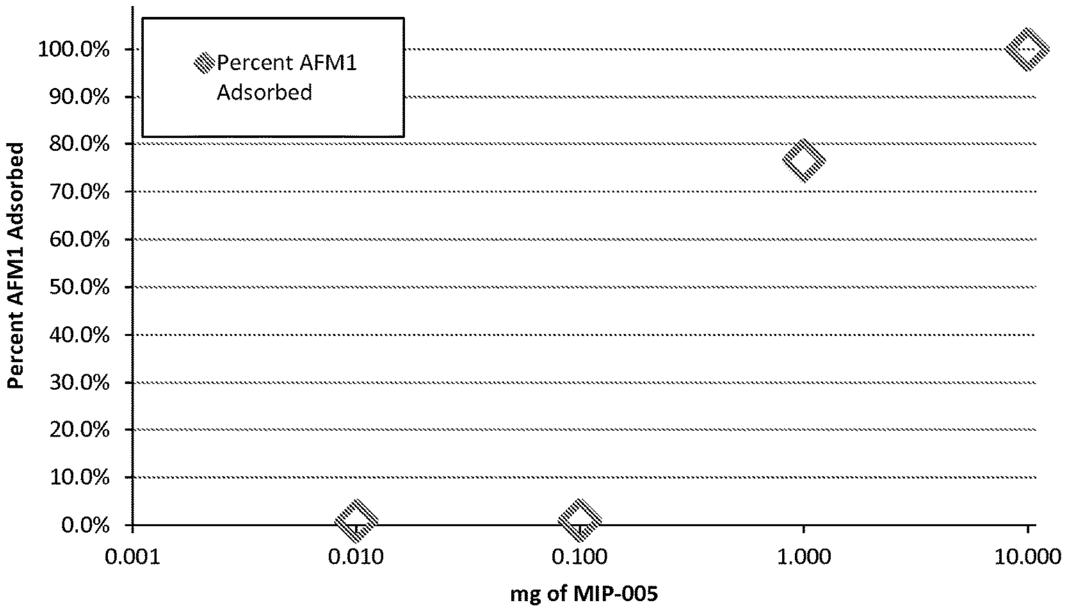
FIG. 5 shows results for the instant trapping of AFM1 by MIP-005 at various inclusion rates (ranging from 0.001%-0.1%) in an SPE column setup at room temperature.

An initial study evaluated the level of inclusion of MIP necessary to sequester AFM1. MIP-005 material was studied in buffer conditions. As shown in the FIG. 5, it was found that 1 mg of powder (representing an inclusion rate of 0.1%, w/v) was able to adsorb 76.5% of the AFM1 from the 100 ng/L AFM1 solution in buffer. Meanwhile the 0.001% and 0.01% (w/v) inclusion rates resulted in negligible AFM1 adsorption. On the other hand, an inclusion rate of 1.0% (w/v) showed 100% adsorption of AFM1. See FIG. 5.

All publications and patents described herein are hereby incorporated by reference.

Those skilled in the art will readily appreciate that many modifications are possible without materially departing from the novel teachings and advantages of this disclosure. Accordingly, all such modifications are intended to be included within the scope of this disclosure as defined in the following claims.

What is claimed is:

1. A molecularly imprinted polymer intermediate, comprising: a crosslinked polymer made from monomers which are chemically bonded to each other, and a template having Formula (I):

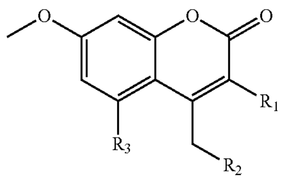

wherein $R_1$ is selected from the group consisting of H, $C_{1-6}$ alkyl, substituted $C_{1-6}$ alkyl, and a halo substituted $C_{1-6}$ alkyl; $R_2$ is selected from the group consisting of halo, $C_{1-6}$ alkyl, substituted $C_{1-6}$ alkyl, a halo substituted $C_{1-6}$ alkyl, $CH_2C(O)OR'$, and $CH(C(O)OR')_2$; wherein R' is selected from the group consisting of H, $C_{1-6}$ alkyl, and substituted $C_{1-6}$ alkyl; and $R_3$ is selected from the group consisting of H, $C_{1-6}$ alkoxy, and substituted $C_{1-6}$ alkyl, or wherein $R_1$ together with $R_2$ form a $C_{4-7}$ cycloalkyl ring, a halo substituted $C_{4-7}$ cycloalkyl ring, an oxo substituted $C_{4-7}$ cycloalkyl ring, a $C_{4-7}$ cycloalkoxy ring, a hydroxy substituted $C_{4-7}$ cycloalkyl ring, or a carboxylic group substituted $C_{4-7}$ cycloalkyl; and $R_3$ is selected from the group consisting of H, $C_{1-6}$ alkoxy, and substituted $C_{1-6}$ alkyl, wherein the crosslinked polymer defines a plurality of cavities, wherein at least one of the cavities comprises the template having Formula (I), and wherein the at least one cavity is sized and/or shaped to allow an aflatoxin to be boundable therein when empty.

2. The molecularly imprinted polymer intermediate of claim 1, wherein the template having Formula (I) is selected from the group consisting of 4-(chloromethyl)-5,7-dimethoxy coumarin, 5,7-dimethoxycyclo pentenon[2,3-c]coumarin, and any combination thereof.

3. The molecularly imprinted polymer intermediate of claim 1, wherein the monomers are methacrylic acid, 2-vinylpyridine, 2-hydroxyethylmethacrylate, or any combination thereof.

4. The molecularly imprinted polymer intermediate of claim 1, wherein the crosslinked polymer comprises a polymer network formed by monomers and a crosslinker.

5. The molecularly imprinted polymer intermediate of claim 1, wherein the template having Formula (I) and the monomers are used in a molar ratio of from about 100:1 to about 1:100.

6. The molecularly imprinted polymer intermediate of claim 4, wherein the monomers and the crosslinker are used in a molar ratio of from about 1:4.1 to about 1:10.

7. The molecularly imprinted polymer intermediate of claim 1, wherein the at least one cavity has a capacity to form a complex with an aflatoxin to bind the aflatoxin therein.

8. The molecularly imprinted polymer intermediate of claim 1, wherein the template having Formula (I) is an isolated compound that has a formula of:

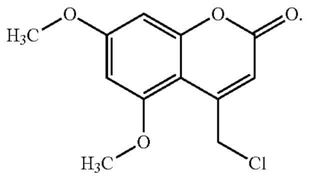 [SMILES: COc1cc(OC)c2c(CCl)cc(=O)oc2c1]

9. The molecularly imprinted polymer intermediate of claim 1, wherein $R_1$ is H; $R_2$ is selected from the group consisting of halo, $CH_2C(O)OR'$, and $CH(C(O)OR')_2$, wherein R' is selected from the group consisting of H or $C_{1-6}$ alkyl; and $R_3$ is a $C_{1-6}$ alkoxy group.

10. The molecularly imprinted polymer intermediate of claim 1, wherein the at least one cavity has complementary shape and stereochemistry to the template having Formula (I) used to make the cavity.

11. The molecularly imprinted polymer intermediate of claim 1, wherein the crosslinked polymer comprises a three-dimensional polymer network formed by monomers and a crosslinker, wherein the monomers and the crosslinker are used in a molar ratio of from about 1:4.1 to about 1:10, wherein the at least one cavity has a capacity to form a complex with an aflatoxin to bind the aflatoxin therein.

12. The molecularly imprinted polymer intermediate of claim 1, wherein the template having Formula (I) is an isolated compound selected from the group consisting of:

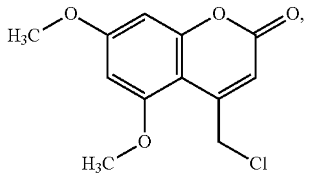

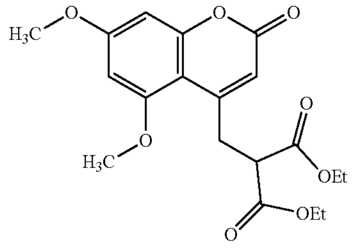

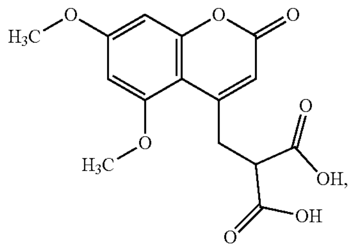

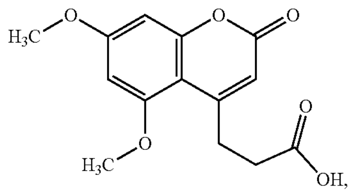

and any combination thereof.

* * * * *